US012673070B2

(12) United States Patent　　(10) Patent No.:　US 12,673,070 B2
Bruce　　(45) Date of Patent:　Jul. 7, 2026

(54) TREATMENT OF SEPSIS AND HYPERCYTOKINEMIA

(71) Applicant: TX MEDIC AB, Viken (SE)

(72) Inventor: Lars Bruce, Viken (SE)

(73) Assignee: TX MEDIC AB, Viken (SE)

( * ) Notice: Subject to any disclaimer, the term of this patent is extended or adjusted under 35 U.S.C. 154(b) by 686 days.

(21) Appl. No.: 17/907,714

(22) PCT Filed: Apr. 14, 2021

(86) PCT No.: PCT/SE2021/050345
§ 371 (c)(1),
(2) Date: Sep. 29, 2022

(87) PCT Pub. No.: WO2021/211044
PCT Pub. Date: Oct. 21, 2021

(65) Prior Publication Data
US 2023/0126862 A1　　Apr. 27, 2023

Related U.S. Application Data

(60) Provisional application No. 63/010,211, filed on Apr. 15, 2020.

(51) Int. Cl.
*A61K 31/737*　　(2006.01)
*A61K 9/00*　　(2006.01)
*A61P 7/00*　　(2006.01)
*A61P 31/00*　　(2006.01)
*A61P 31/14*　　(2006.01)

(52) U.S. Cl.
CPC .......... *A61K 31/737* (2013.01); *A61K 9/0019* (2013.01); *A61P 7/00* (2018.01); *A61P 31/00* (2018.01); *A61P 31/14* (2018.01)

(58) Field of Classification Search
CPC .......................... C08B 37/0021; A61K 31/737
See application file for complete search history.

(56) References Cited

U.S. PATENT DOCUMENTS

| | | | |
|---|---|---|---|
| 8,901,104 B2 * | 12/2014 | Nilsson ................... | A61P 37/06 514/59 |
| 10,307,440 B2 | 6/2019 | Nilsson et al. | |
| 10,407,514 B2 | 9/2019 | Bruce et al. | |
| 10,730,960 B2 * | 8/2020 | Bruce ................. | C08B 37/0021 |
| 11,530,270 B2 | 12/2022 | Wang et al. | |
| 2004/0009953 A1 * | 1/2004 | Comper ............... | A61K 31/715 514/54 |
| 2010/0087393 A1 | 4/2010 | Bansal | |
| 2021/0060057 A1 | 3/2021 | Bruce | |
| 2023/0346827 A1 * | 11/2023 | Bruce ....................... | A61P 7/04 |

FOREIGN PATENT DOCUMENTS

| | | |
|---|---|---|
| CN | 1717240 A | 1/2006 |
| CN | 107106595 A | 8/2017 |
| EP | 0868191 A1 | 10/1998 |
| JP | 8-92103 A | 4/1996 |
| JP | 2000-507204 A | 6/2000 |
| JP | 2006-509057 A | 3/2006 |
| JP | 2018-501332 A | 1/2018 |
| JP | 2020-508657 A | 3/2020 |
| WO | 97/22347 A1 | 6/1997 |
| WO | 2008/134430 A1 | 11/2008 |
| WO | WO-2016076780 A1 * | 5/2016 .......... A61K 31/721 |
| WO | 2019/050460 A1 | 3/2019 |
| WO | 2020/256627 A1 | 12/2020 |

OTHER PUBLICATIONS

Peng et al., "Inhibition of Inflammatory Cytokine-Induced Response to HUman Islet Cells by Withaferin A" Transplantation Proceedings vol. 42 pp. 2058-2061, DOI:10.1016/j.transproceed.2010.05.131 (Year: 2010).*

Channappanavar et al., "Pathogenic human coronavirus infections: causes and consequences of cytokine storm and immunopathology" Semin Immunopathol vol. 39 pp. 529-539, DOI 10.1007/s00281-017-0629-x (Year: 2017).*

Burger et al., "Dextran Sulfate: Influence of Molecular Size and Degree of Sulfation on the Activation of Complement via the Alternative Pathway" Immunology vol. 34 No. 3, p. 981 (Year: 1975).*

Search report from corresponding European Application No. 21788142.4 dated Mar. 19, 2024.

Office Action dated Apr. 15, 2025 from corresponding Japanese Application No. 2022-562955, pp. 1-10.

Mollnes, Tom E. et al., Complement in sepsis—when science meets clinics, FEBS Letters, vol. 594, pp. 2621-2632 (online Jul. 21, 2020).

Petrak, MD, Russell M. et al., Early Tocilizumab Dosing Is Associated With Improved Survival in Critically Ill Patients Infected With Severe Acute Respiratory Syndrome Coronavirus-2, Critical Care Explorations, vol. 3, No. 1, pp. 1-6 (Apr. 2021).

Petrak, MD, Russell M. et al., Early Tocilizumab Dosing Is Associated With Improved Survival in Critically Ill Patients Infected With Severe Acute Respiratory Syndrome Coronavirus-2, Critical Care Explorations, vol. 3, No. 1, pp. 1-6 (Oct. 28, 2020, preprint).

Ricklin, Daniel et al., Complement in immune and inflammatory disorders: therapeutic interventions, J Immunol, vol. 190(8), pp. 3839-3847 (Apr. 15, 2013).

Rodrigues, Patricia R.S. et al., Sepsis target validation for repurposing and combining complement and immune checkpoint inhibition therapeutics, Expert Opinion on Drug Discovery, vol. 16, No. 5, pp. 537-551 (online Dec. 14, 2020).

Office Action dated Jul. 31, 2025 from corresponding Israeli Patent Application No. 296600. 7 pages.

(Continued)

*Primary Examiner* — Andrea Olson

(74) *Attorney, Agent, or Firm* — Porter Wright Morris & Arthur LLP

(57) ABSTRACT

The invention relates to dextran sulfate, or a pharmaceutically acceptable salt thereof, in treatment of sepsis and hypercytokinemia.

17 Claims, 17 Drawing Sheets

(56)                    References Cited

OTHER PUBLICATIONS

Examination Report dated Jan. 30, 2026 from corresponding Australian Application No. 2021255662, pp. 1-4.

Lazzarino, Giacomo et al., Low Molecular Weight Dextran Sulfate (ILB®) Administration Restores Brain Energy Metabolism Following Severe Traumatic Brain Injury in the Rat, Antioxidants, vol. 9, No. 850, pp. 1-18 (2020).

Office Action dated Nov. 4, 2025 from corresponding Chinese Application No. 2021800341837, with English Translation, pp. 1-11.

Office Action dated Oct. 30, 2025 from corresponding European Application No. 21788142.4, pp. 1-5.

Office Action dated Feb. 25, 2026 from corresponding Canadian Application No. 3,174,935, pp. 1-6.

\* cited by examiner

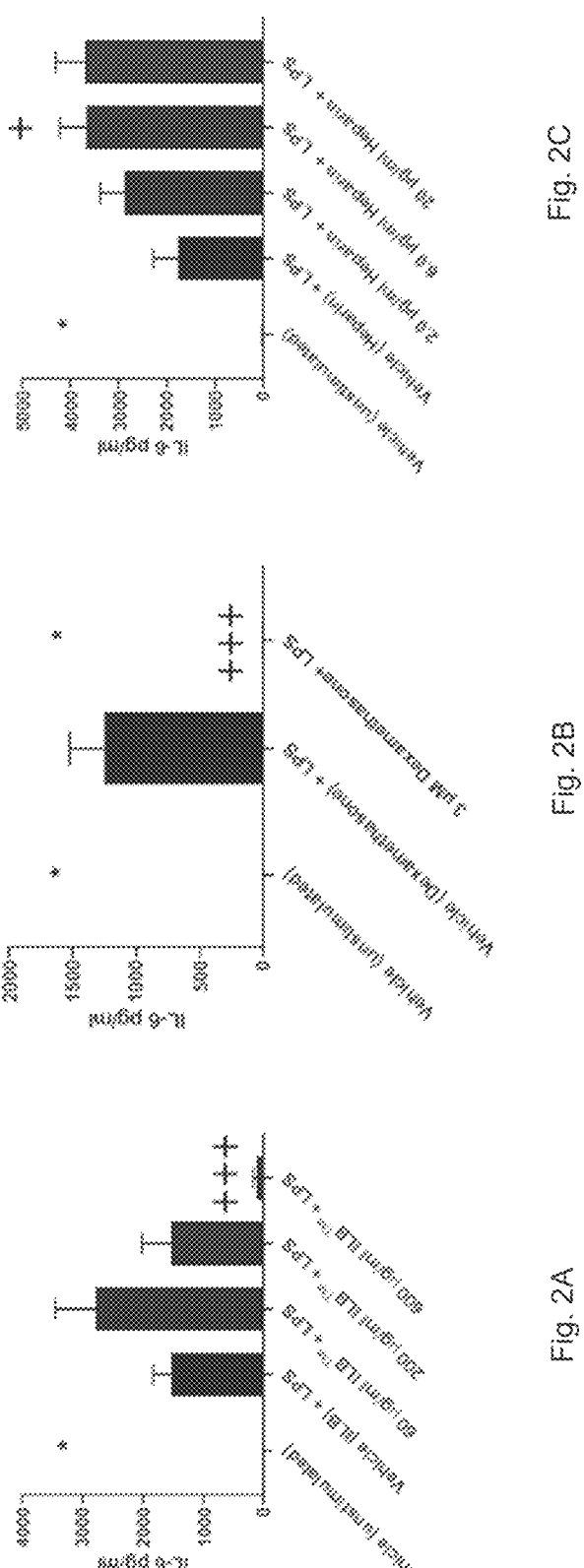

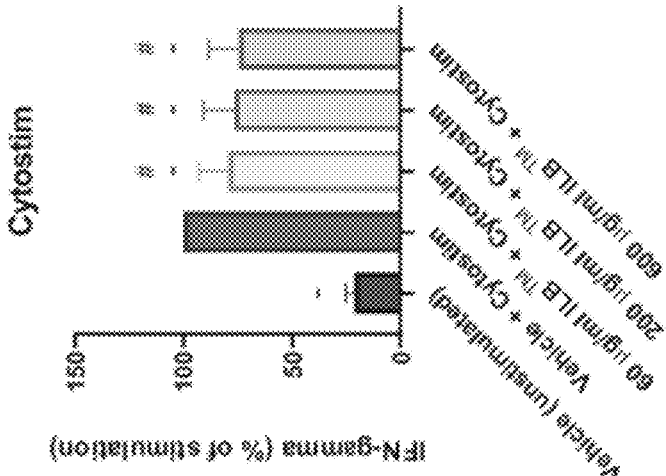
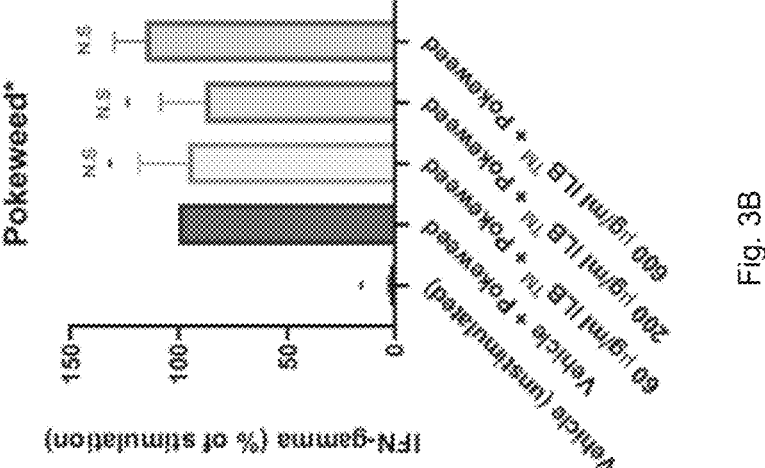
Fig. 3B
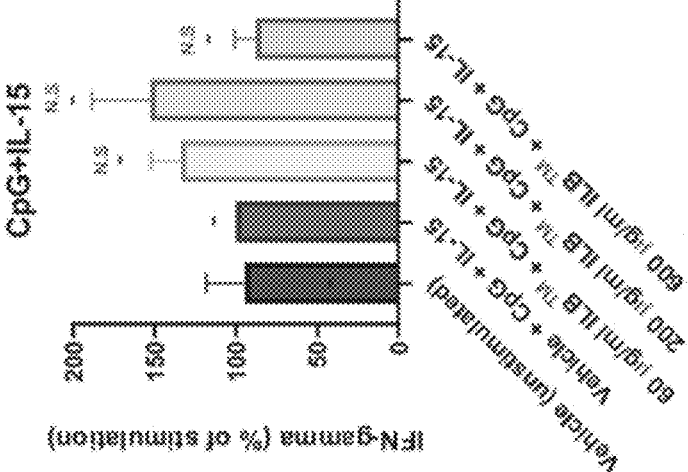

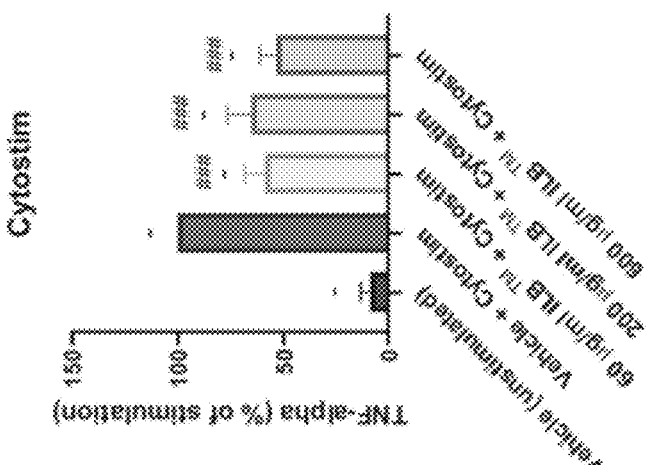
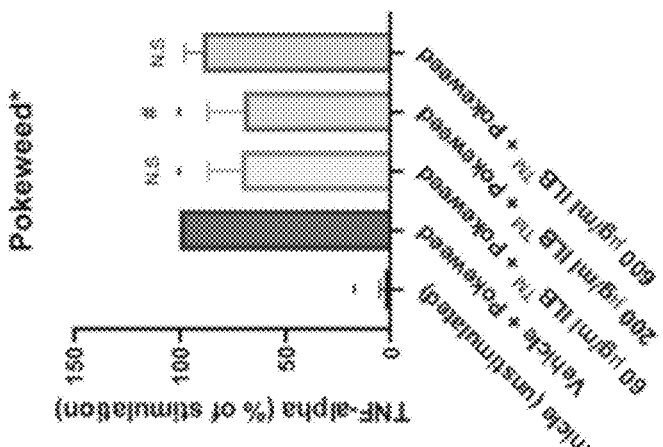
Fig. 5B
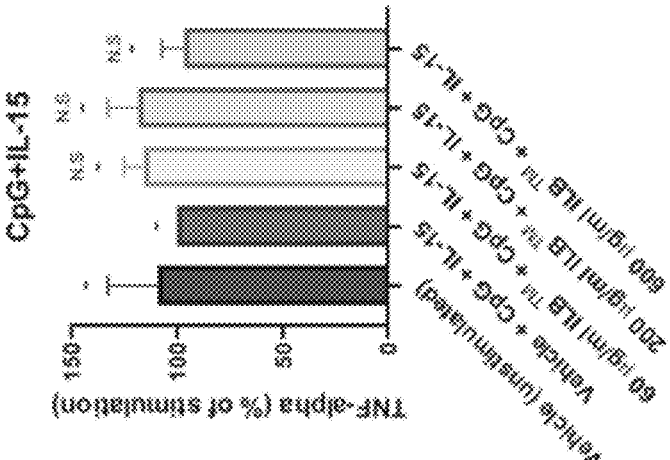

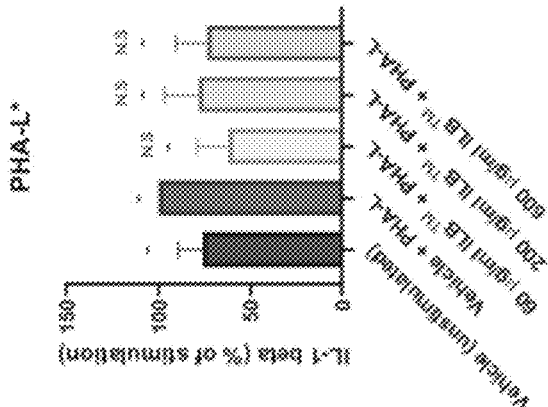
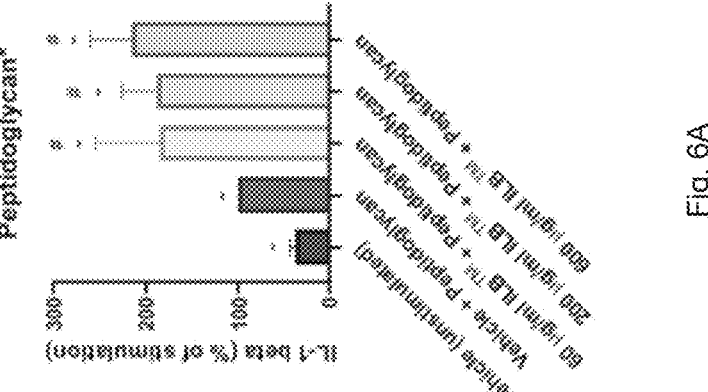
Fig. 6A
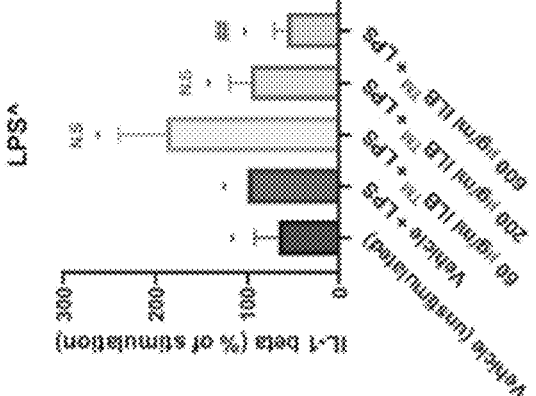

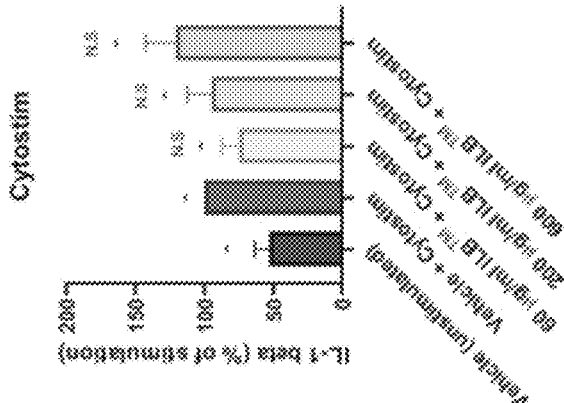
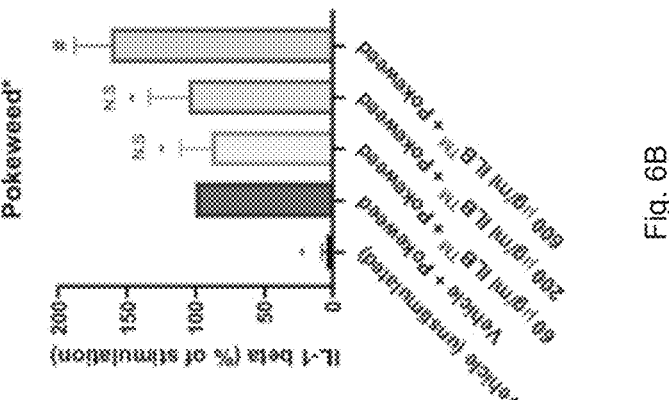
Fig. 6B
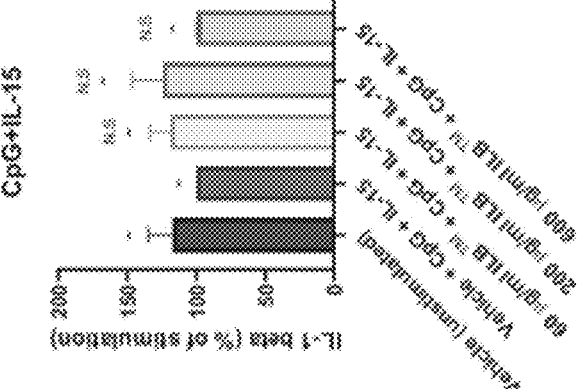

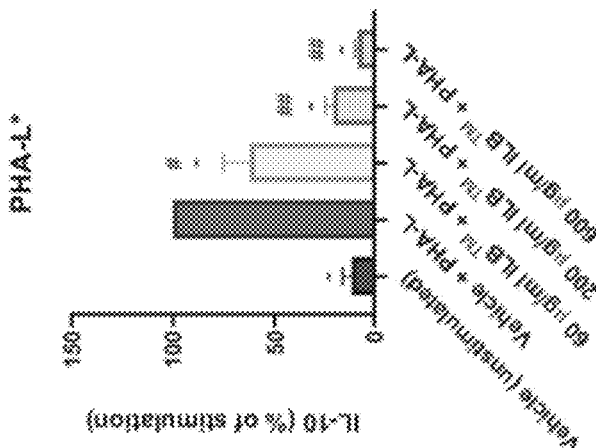
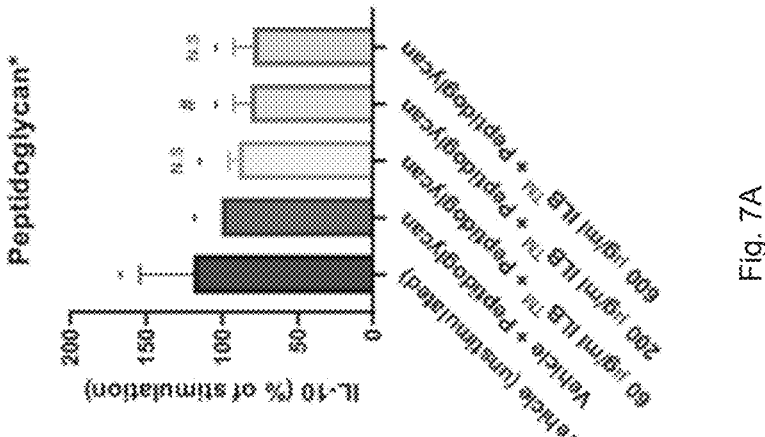
Fig. 7A
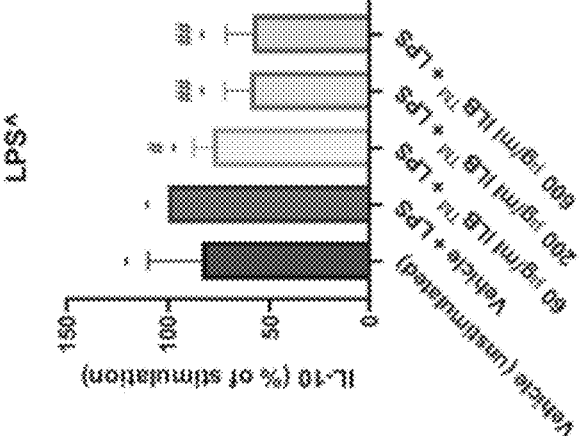

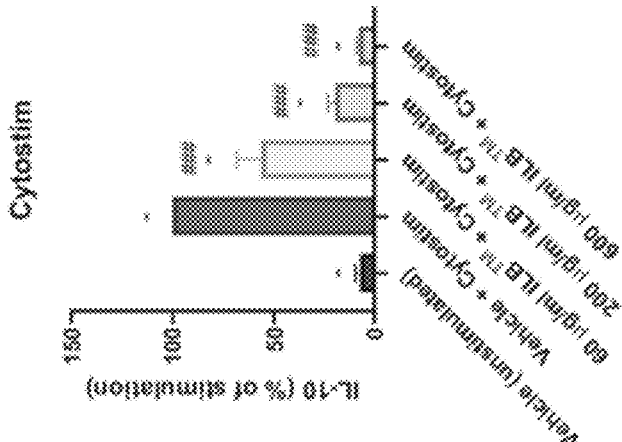
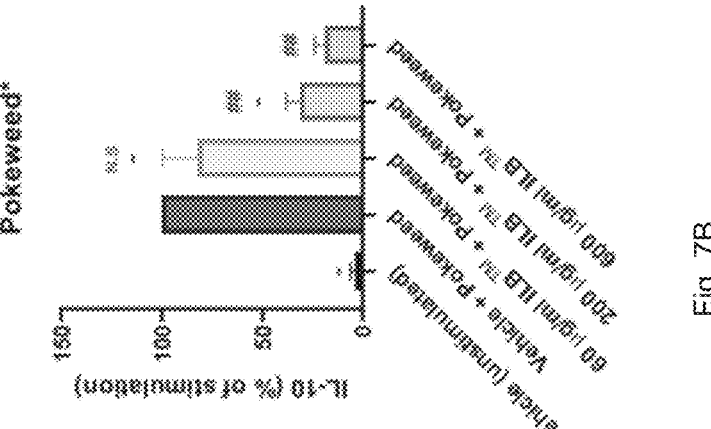
Fig. 7B
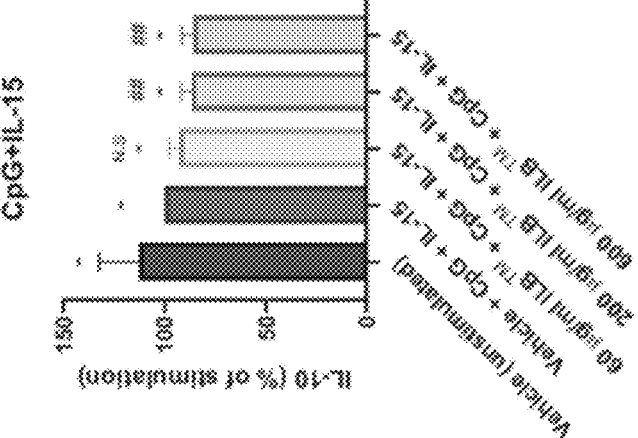

TREATMENT OF SEPSIS AND HYPERCYTOKINEMIA

TECHNICAL FIELD

The present invention generally relates to treatment of sepsis and hypercytokinemia, and in particular to the use of dextran sulfate, or a pharmaceutically acceptable salt thereof, in treatment of sepsis and hypercytokinemia.

BACKGROUND

Sepsis is a life-threatening condition that arises when the body's response to infection causes injury to its own tissues and organs. Sepsis is an inflammatory immune response triggered by an infection. Bacterial infections are the most common cause, but fungal, viral, and protozoan infections can also lead to sepsis. Common locations for the primary infection include the lungs, brain, urinary tract, skin, and abdominal organs.

Hypercytokinemia, also referred to as cytokine storm, is a physiological reaction, in which the innate immune system causes an uncontrolled and excessive release of pro-inflammatory cytokines. Hypercytokinemia can be caused by a number of infectious and non-infectious etiologies, in particular viral infections.

Cytokines are regulators of the immune response to infection and play a key role in regulating inflammation and trauma. Pro-inflammatory cytokines stimulate systematic inflammation, whereas anti-inflammatory cytokines inhibit inflammation and enhance healing. The major pro-inflammatory cytokines that regulate early responses in sepsis include interleukin-1α (IL-1α), IL-1β, IL-6, and tumor necrosis factor-α (TNFα). Pro-inflammatory cytokines act as endogenous pyrogens, up-regulate the synthesis of secondary mediators and other pro-inflammatory cytokines by both macrophages and mesenchymal cells, such as fibroblasts, epithelial and endothelial cells, and stimulate the production of acute phase proteins, or attract inflammatory cells.

Sepsis is characterized by the excessive production of cytokines in the circulating blood, leading to a cytokine storm (hypercytokinemia) and systematic inflammatory response. Therefore, inhibition of excessive cytokine production or removal of cytokines and other inflammatory mediators from the blood have been suggested to suppress systemic inflammation during sepsis and hypercytokinemia and improve patient outcomes.

Corticosteroids have been used to treat sepsis by suppressing cytokine production. A major disadvantage with corticosteroids is the broad effect, generally suppressing cytokine production of both pro-inflammatory and anti-inflammatory cytokines. In addition, the suppression may be hard to control, possibly leading to too low levels of cytokines and thereby failure by the patient's immune system to combat the infection that is the underlying cause of the sepsis or hypercytokinemia.

Another group of drugs suggested for sepsis treatments is neutralizing antibodies. A shortcoming of this group of drugs is their specificity, targeting a single cytokine. The activities of other cytokines are thereby left untouched or may indeed increase due to compensating mechanisms. Another disadvantage of antibodies is their relative long half lives in the body. As a consequence, their cytokine blocking effect may extend over comparatively long periods of time, and may in fact be too long in order to successfully combat the sepsis or hypercytokinemia causing infection by the patient's immune system.

Hence, there is still a need for an effective treatment of sepsis and hypercytokinemia.

SUMMARY

It is an objective to provide a treatment of sepsis.

It is another objective to provide treatment of hypercytokinemia.

These and other objectives are met by embodiments as disclosed herein.

An aspect of the invention relates to dextran sulfate, or a pharmaceutically acceptable salt thereof, for use in treatment of sepsis.

Another aspect of the invention relates to dextran sulfate, or a pharmaceutically acceptable salt thereof, for use in treatment of hypercytokinemia.

Dextran sulfate, or the pharmaceutically acceptable salt thereof, is capable of suppressing pro-inflammatory cytokines in selected immune cells. This means that dextran sulfate, or the pharmaceutically acceptable salt thereof, prevents or at least significantly inhibits the increased levels of these cytokines in the circulating blood causing a cytokine storm and systematic inflammatory response in patients. The cytokine suppression as achieved by dextran sulfate, or the pharmaceutically acceptable salt thereof, still enables the patient's immune system to remain active and combat the infection, which is the underlying cause of sepsis or hypercytokinemia.

BRIEF DESCRIPTION OF THE DRAWINGS

The embodiments, together with further objects and advantages thereof, may best be understood by making reference to the following description taken together with the accompanying drawings, in which:

FIGS. 2A-2F Monocytes purified from PBMCs were cultured in the absence of stimulation (media) or stimulated with LPS (0.01 ng/ml) or peptidoglycan (30 ng/ml) in the absence (Vehicle) or presence of either (2A, 2D) LMW-DS (ILB™; 60 μg/ml, 200 μg/ml or 600 μg/ml), (2B, 2E) dexamethasone (3.0 μM) or (2C, 2F) heparin (2.0 μg/ml, 6.0 μg/ml or 20 μg/ml) for 24 hours. Levels of IL-6 were quantified in the cell culture supernatant by ELISA. Data presented as mean±SEM, n=10. * indicates below the limit of detection (5 μg/ml). +P<0.05, +++P<0.001 Significant difference to stimulation (Mann Whitney U Test).

FIGS. 3A and 3B PBMCs were cultured in the absence (media, unstimulated) or presence of stimulus: LPS (0.01 ng/ml), peptidoglycan (30 ng/ml), PHA-L (1.0 μg/ml), CpG (0.2 μM)+IL-15 (15 ng/ml), pokeweed mitogen (1.0 μg/ml) or Cytostim (10 μl/ml) plus vehicle (0.027% saline) or LMW-DS (ILB™ at 60 μg/ml, 200 μg/ml or 600 μg/ml) for 24 hours. Levels of interferon gamma (IFNγ) were quantified in the supernatant by Luminex. Data presented as percentage stimulus+vehicle and mean±SEM from 12 donors unless otherwise indicated. (−) Indicates at least one replicate was below the limit of quantification, (+) indicates at least one replicate was above the limit of quantification, (ˆ) indicates data from 11 donors and (*) indicates data from 6 donors. Comparison to stimulation with vehicle: #P<0.05, ##P<0.01, ###P<0.001 and N.S indicates not-significant (Mann Whitney test, two tailed).

FIGS. 5A and 5B PBMCs were cultured in the absence (media, unstimulated) or presence of stimulus: LPS (0.01 ng/ml), peptidoglycan (30 ng/ml), PHA-L (1.0 μg/ml), CpG (0.2 μM)+IL-15 (15 ng/ml), pokeweed mitogen (1.0 μg/ml) or Cytostim (10 μl/ml) plus vehicle (0.027% saline) or LMW-DS (ILB™ at 60 μg/ml, 200 μg/ml or 600 μg/ml) for 24 hours. Levels of tumor necrosis factor alpha (TNFα) were quantified in the supernatant by Luminex. Data presented as percentage stimulus+vehicle and mean±SEM from 12 donors unless otherwise indicated. (−) Indicates at least one replicate was below the limit of quantification, (+) indicates at least one replicate was above the limit of quantification, (ˆ) indicates data from 11 donors and (*) indicates data from 6 donors. Comparison to stimulation with vehicle: #P<0.05, ##P<0.01, ###P<0.001 and N.S indicates not-significant (Mann Whitney test, two tailed).

FIGS. 6A and 6B PBMCs were cultured in the absence (media, unstimulated) or presence of stimulus: LPS (0.01 ng/ml), peptidoglycan (30 ng/ml), PHA-L (1.0 μg/ml), CpG (0.2 μM)+IL-15 (15 ng/ml), pokeweed mitogen (1.0 μg/ml) or Cytostim (10 μl/ml) plus vehicle (0.027% saline) or LMW-DS (ILB™ at 60 μg/ml, 200 μg/ml or 600 μg/ml) for 24 hours. Levels of IL-1β were quantified in the supernatant by Luminex. Data presented as percentage stimulus+vehicle and mean±SEM from 12 donors unless otherwise indicated. (−) Indicates at least one replicate was below the limit of quantification, (+) indicates at least one replicate was above the limit of quantification, (ˆ) indicates data from 11 donors and (*) indicates data from 6 donors. Comparison to stimulation with vehicle: #P<0.05, ##P<0.01, ###P<0.001 and N.S indicates not-significant (Mann Whitney test, two tailed).

FIGS. 7A and 7B PBMCs were cultured in the absence (media, unstimulated) or presence of stimulus: LPS (0.01 ng/ml), peptidoglycan (30 ng/ml), PHA-L (1.0 μg/ml), CpG (0.2 μM)+IL-15 (15 ng/ml), pokeweed mitogen (1.0 μg/ml) or Cytostim (10 μl/ml) plus vehicle (0.027% saline) or LMW-DS (ILB™ at 60 μg/ml, 200 μg/ml or 600 μg/ml) for 24 hours. Levels of IL-10 were quantified in the supernatant by Luminex. Data presented as percentage stimulus+vehicle and mean±SEM from 12 donors unless otherwise indicated. (−) Indicates at least one replicate was below the limit of quantification, (+) indicates at least one replicate was above the limit of quantification, (ˆ) indicates data from 11 donors and (*) indicates data from 6 donors. Comparison to stimulation with vehicle: #P<0.05, ##P<0.01, ###P<0.001 and N.S indicates not-significant (Mann Whitney test, two tailed).

DETAILED DESCRIPTION

Figure 1B:
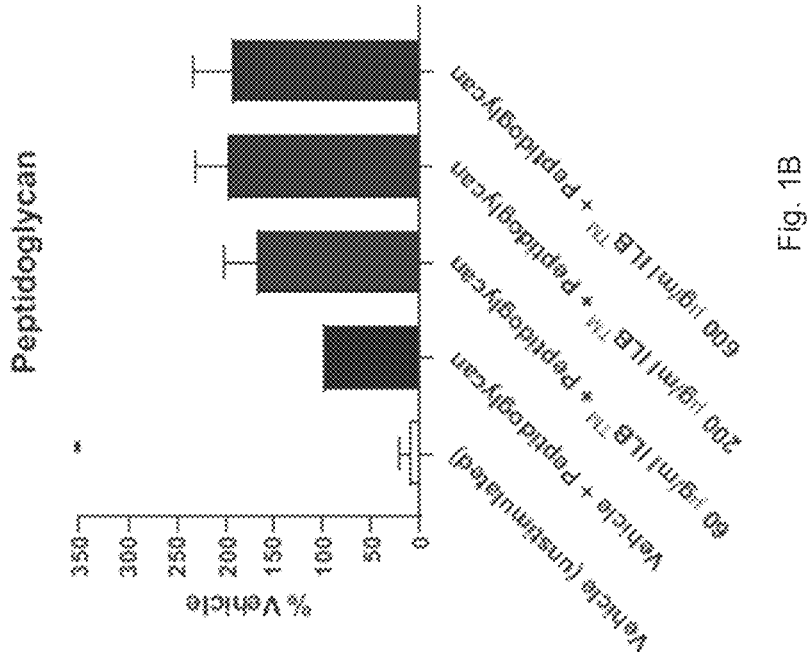
FIGS. 1A-1H PBMC were cultured in the absence (media, unstimulated) or presence of stimulus: (1A) LPS (0.01 ng/ml), (1B) peptidoglycan (30 ng/ml), (1C) pokeweed mitogen (1.0 μg/ml) (1D) PHA-L (1.0 μg/ml), (1E, 1F) CpG (0.2 μM or 1.0 μM)+IL-15 (15 ng/ml), or (1G, 1H) cytostim (10 μl/ml or 30 μl/ml) plus vehicle (0.027% saline) or LMW-DS (ILB™ at either 60 μg/ml, 200 μg/ml or 600 μg/ml) for 24 hours. Levels of IL-6 were quantified in the supernatant by ELISA. Data presented as mean±SEM arising from six to twelve (LPS) donors. Data plotted as percentage stimulus+vehicle. (−) indicates at least one donor was below the limit of detection. **Mann-Whitney U test comparison between Vehicle+LPS and 600 μg/ml ILB™+ LPS p=0.005. *MannWhitney U test comparison between Vehicle+PHA-L and 600 μg/ml ILB™+PHA-L p=0.048.

The present invention generally relates to treatment of sepsis or hypercytokinemia, and in particular to the use of dextran sulfate, or a pharmaceutically salt thereof, in treatment of sepsis or hypercytokinemia.

Traditionally, sepsis is defined as systemic inflammatory response syndrome (SIRS) in response to an infectious process. SIRS is the presence of two or more of the following: abnormal body temperature (<36° C. or >38° C.), abnormal heart rate (>90 beats/min), abnormal respiratory rate (>20/min), or abnormal blood gas (PaCO$_2$<32 mmgH), and white blood cell (WBC) count (<4000/mm$^3$ or >12,000/mm$^3$). Severe sepsis is defined as sepsis with sepsis-induced organ dysfunction or tissue hypoperfusion (manifesting as hypotension, elevated lactate, or decreased urine output). Severe sepsis is an infectious disease state associated with multiple organ dysfunction syndrome (MODS). Septic shock is severe sepsis plus persistently low blood pressure, despite the administration of intravenous fluids.

Sepsis is characterized by the excessive production of cytokines in the circulating blood causing a cytokine storm (hypercytokinemia), leading to a systematic inflammatory response. Therefore, inhibition of excessive cytokine production or removal of cytokines and other inflammatory mediators from the blood have been suggested to suppress the cytokine storm and systemic inflammation during sepsis and improve patient outcomes. However, one challenge in sepsis and hypercytokinemia is how to target elements of a response without generating prolonged immunosuppression or complete immunosuppression.

Hypercytokinemia or cytokine storm is a physiological reaction in humans and other animals, in which the innate immune system causes uncontrolled and excessive release of pro-inflammatory cytokines. Cytokine storms can be caused by a number of infectious and non-infectious etiologies, especially viral respiratory infections, such as influenza A virus subtype H5N1, severe acute respiratory syndrome coronavirus (SARS-CoV-1) and SARS-CoV-2. Other causative agents include the Epstein-Barr virus, cytomegalovirus, and group A *streptococcus*, and non-infectious conditions such as graft-versus-host disease. The viruses can invade lung epithelial cells and alveolar macrophages to produce viral nucleic acids, which stimulate the infected cells to release cytokines and chemokines, activating, among others, macrophages and dendritic cells, to release additional cytokines resulting in a cytokine storm.

Dextran sulfate, or a pharmaceutically acceptable salt thereof, is capable of selectively reducing levels of pro-inflammatory cytokines, in particular interleukin 6 (IL-6)

but also tumor necrosis factor alpha (TNFα), IL-1β, IL-8, and interferon gamma (IFNγ). This suppression of cytokine levels is particularly induced in toll-like receptor (TLR) 4 activated monocytes, macrophages and microglia (myeloid cells). Such TLR4-based activation of myeloid cells is of importance in the case of bacterial infections, including gram negative bacterial infections since TLR4 constitutes a sensing receptor for gram-negative lipopolysaccharides (LPS). Other TLR4 ligands include F protein of syncytial virus, mannuronic acid from gram negative bacteria, teichuronic acid from gram positive bacteria, *Chlamydia pneumoniae* HSP60, flavolipin from *Flavobacterium meningosepticum*, mannan from *Saccharomyces cerevisiae* and *Candida albicans*, and Dengue virus NS1 protein. TLR4 activation of myeloid cells is seen in patients suffering from cytokine storm and sepsis.

Hence, reducing pro-inflammatory cytokines in patients suffering from infectious diseases, hypercytokinemia and/or sepsis by dextran sulfate, or the pharmaceutically acceptable salt thereof, leads to a suppression of the cytokine storm and of the systemic inflammation during sepsis and will improve patient outcomes.

Dextran sulfate, or the pharmaceutically acceptable salt thereof, has advantageous over current drugs employed to treat sepsis and hypercytokinemia, including corticosteroids and neutralizing anti-cytokine antibodies.

Figures 2D, 2E, 2F:
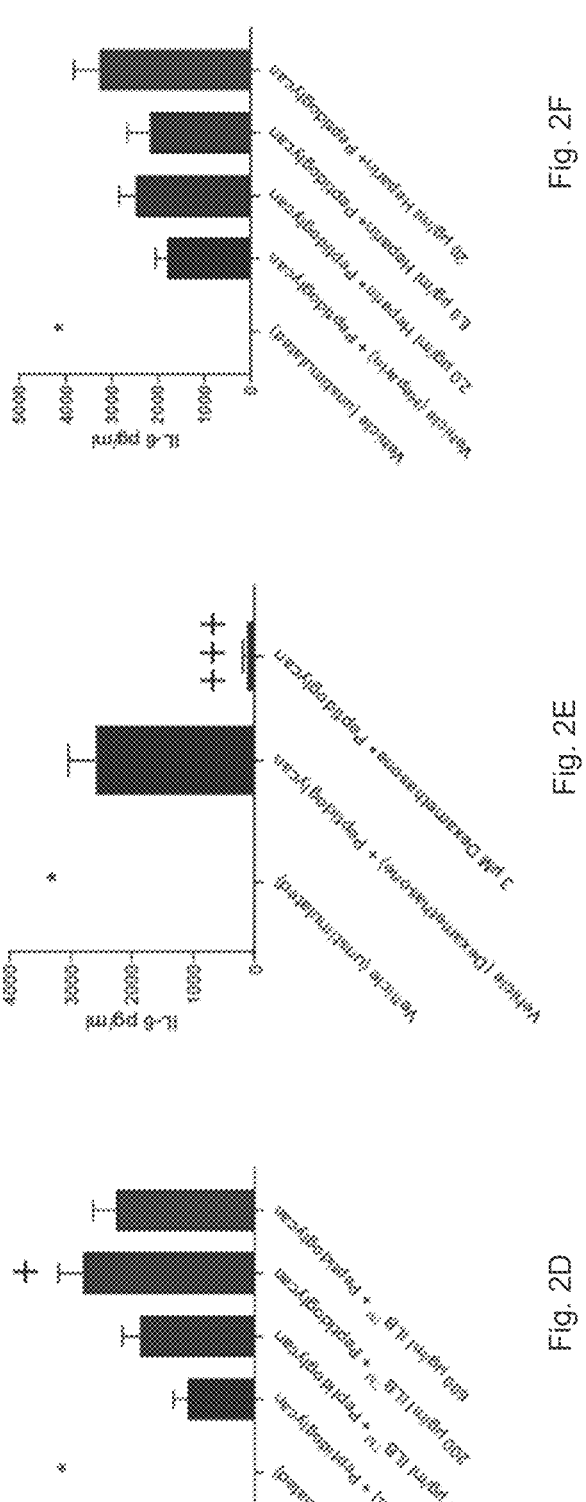

Firstly, corticosteroids have a broad effect generally suppressing cytokine production of both pro-inflammatory and anti-inflammatory cytokines. Furthermore, the suppression is almost complete as shown in FIGS. 2B and 2E. Such total immune suppression may, however, actually be detrimental to the sepsis patients since the immune system is thereby severely inhibited, thereby reducing its effectiveness in combating the infectious disease that is the underlying cause of the hypercytokinemia or sepsis.

Experimental data as presented herein shows that dextran sulfate, or the pharmaceutically acceptable salt thereof, does not fully shut-off cytokine activity and moreover does not suppress cytokine levels from all cells of the immune system (FIGS. 1A-1H, 3A-7B). This means that dextran sulfate, or the pharmaceutically acceptable salt thereof, can be useful in treating hypercytokinemia or sepsis by reducing pro-inflammatory cytokine levels, while at the same time enabling activation of the immune system to combat the infection that is the underlying cause of hypercytokinemia or sepsis.

For instance, experimental data indicates that dextran sulfate is able to suppress IL-6 cytokine production by activated cells in the innate immune system, in particular myeloid cells, such as monocytes and macrophages, (FIG. 1A), while not significantly affecting IL-6 cytokine production by activated cells in the acquired immune system, such as B lymphocytes (FIGS. 1B, 1C, 1F, 1H).

Furthermore, the IL-6 suppressing effect of dextran sulfate, or the pharmaceutically acceptable salt, is not a general effect among sulfated polysaccharides. Experimental data as presented herein showed that heparin, another sulfated polysaccharide, did not significantly suppress IL-6 levels in LPS activated monocytes but rather increased the levels of this pro-inflammatory cytokine (FIG. 2C).

Dextran sulfate, or the pharmaceutically acceptable salt thereof, also has advantages over neutralizing antibodies that have been suggested as treatments of sepsis. Such neutralizing antibodies have a disadvantage in only targeting a single cytokine. This means that activities of other cytokines are thereby left untouched or may indeed increase due to compensating mechanisms. Another disadvantage of antibodies is their relative long half lives in the body (up to two weeks). As a consequence, their cytokine activity blocking effect may extend over comparatively long periods of time, and may in fact be too long in order to successfully combat the hypercytokinemia- or sepsis-causing infection by the patient's immune system. Dextran sulfate, or the pharmaceutically acceptable salt thereof, have a comparatively much shorter half-life ($C_{max}$ is about 2 to 3 hours in humans), thereby simplifying dosing and administration to achieve cytokine suppression during a well-defined period of time when it is needed, while allowing the immune system to combat the hypercytokinemia- or sepsis-causing infection once the acute septic phase has passed.

IL-1β, also known as leukocytic pyrogen, leukocytic endogenous mediator, mononuclear cell factor, lymphocyte activating factor, or catabolin, is produced by activated macrophages as a proprotein, which is proteolytically processed to its active form by caspase-1. IL-1β is an important mediator of the inflammatory response, and is involved in a variety of cellular activities, including cell proliferation, differentiation, and apoptosis. IL-1β has been reported to play a role in sepsis and exhibits persistent increases in patients dying from sepsis (Mera et al., Multiplex cytokine profiling in patients with sepsis, *APMIS*, 119(2): 155-163 (2011)).

Dextran sulfate, or the pharmaceutically acceptable salt thereof, induced a reduction in the LPS stimulated secretion of IL-1β (FIGS. 6A and 6B).

IL-6, also known as interferon-β2 and B-cell stimulatory factor-2 (BSF-2), is a pleiotropic interleukin, and functions as both a pro-inflammatory and anti-inflammatory cytokine. IL-6 is secreted by T cells and macrophages to stimulate the immune response to tissue damage leading to inflammation. IL-6 is also secreted by macrophages in response to specific microbial molecules, referred to as pathogen associated molecular patterns (PAMPs) binding to pattern recognition receptors (PRRs), including toll-like receptors (TLRs). IL-6 production is elevated in patients with sepsis (Mera et al., (2011); Gouel-Cheron et al., Early interleukin-6 and slope of monocyte human leukocyte antigen-DR: A powerful association to predict the development of sepsis after major trauma, *PloS one*, 7(3): e33095 (2012)), indicating that IL-6 is associated with the development of sepsis. Furthermore, the IL-6 level in patients with septic shock is higher than that in patients without septic shock, and higher in those who died from severe sepsis (Wu et al., Serial cytokine levels in patients with severe sepsis, Inflammation Research, 58(7): 385-393 (2009)), suggesting that IL-6 is the key cytokine in the pathophysiology of severe sepsis. In addition, an increased level of IL-6 was found to be associated with the highest risk of death in patients with sepsis (Kellum et al., Understanding the inflammatory cytokine response in pneumonia and sepsis: Results of the Genetic and Inflammatory Markers of Sepsis (GenIMS) Study, *Archives of Internal Medicine*, 167(15): 1655-1663 (2007)). Among the milieu of cytokines induced during sepsis, plasma IL-6 has the best correlation with mortality rate (Kumar et al., Cytokine profile in elderly patients with sepsis, *Indian Journal of Critical Care Medicine*, 13(2): 74-78 (2009)).

Figure 1A:
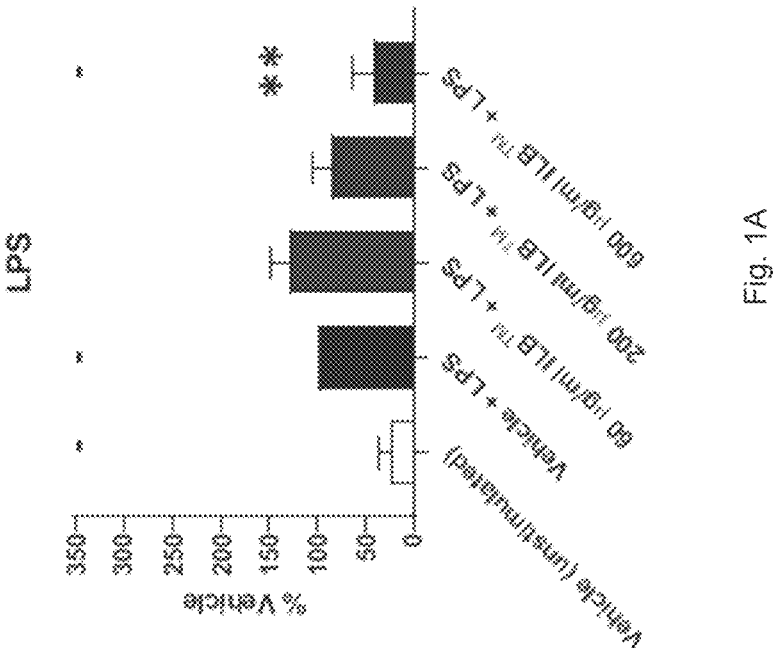

Dextran sulfate, or the pharmaceutically acceptable salt thereof, induced a concentration dependent reduction in the LPS stimulated secretion of IL-6 (FIGS. 1A, 2A).

IL-8, also referred to as chemokine (C—X—C motif) ligand 8 (CXCL8), is a chemokine produced by, among others, macrophages. IL-8 is one of the major mediators of the inflammatory response. Its primary function is the induction of chemotaxis in its target cells, e.g., neutrophil granulocytes. IL-8 serves as a chemical signal that attracts neutrophils to the site of inflammation. Serum and plasma levels of IL-8 are enhanced in patients with sepsis (Livaditi et al., Neutrophil CD64 expression and serum IL-8: Sensitive early markers of severity and outcome in sepsis, Cytokine, 36(5-6): 283-290 (2006)). Furthermore, the initial levels of IL-8 were the most predictive factor for death in patients with sepsis (Mera et al., (2011)), indicating that IL-8 plays a role in sepsis.

Figure 4A:
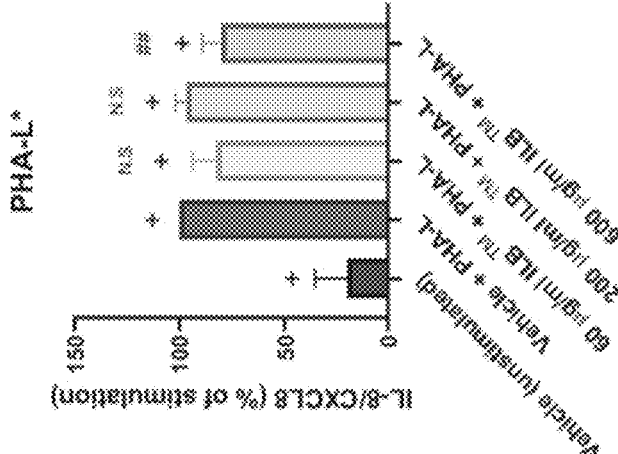
FIGS. 4A and 4B PBMCs were cultured in the absence (media, unstimulated) or presence of stimulus: LPS (0.01 ng/ml), peptidoglycan (30 ng/ml), PHA-L (1.0 μg/ml), CpG (0.2 μM)+IL-15 (15 ng/ml), pokeweed mitogen (1.0 μg/ml) or Cytostim (10 μl/ml) plus vehicle (0.027% saline) or LMW-DS (ILB™ at 60 μg/ml, 200 μg/ml or 600 μg/ml) for 24 hours. Levels of interleukin 8/chemokine (C—X—C motif) ligand 8 (IL-8/CXCL8) were quantified in the supernatant by Luminex. Data presented as percentage stimulus+vehicle and mean±SEM from 12 donors unless otherwise indicated. (−) Indicates at least one replicate was below the limit of quantification, (+) indicates at least one replicate was above the limit of quantification, (ˆ) indicates data from 11 donors and (*) indicates data from 6 donors. Comparison to stimulation with vehicle: #P<0.05, ##P<0.01, ###P<0.001 and N.S indicates not-significant (Mann Whitney test, two tailed).
Figure 4A:
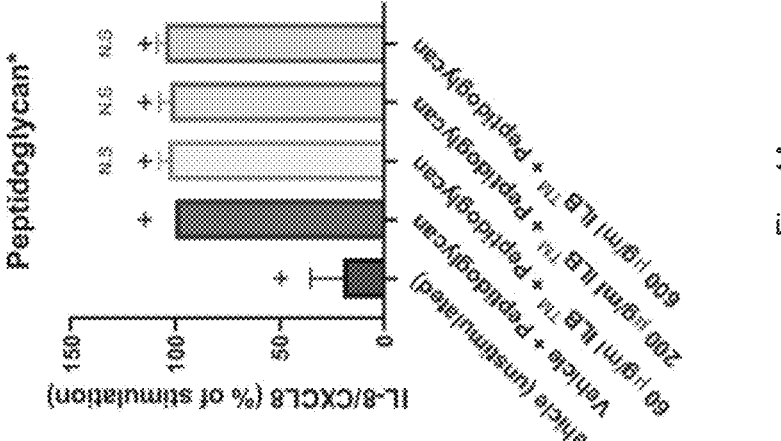
Figure 4A:
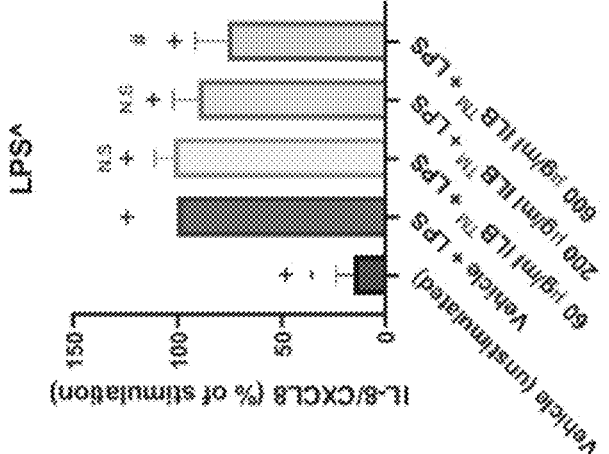
Figure 4B:
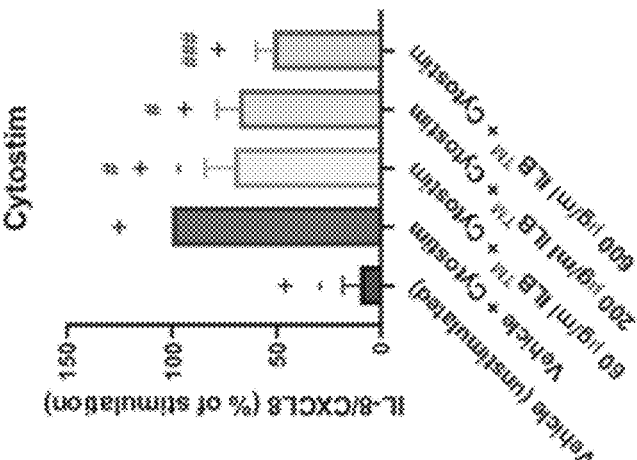
Figure 4B:
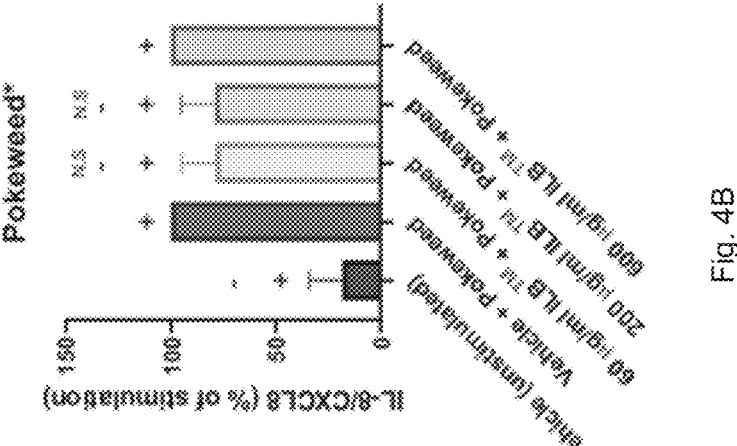
Figure 4B:
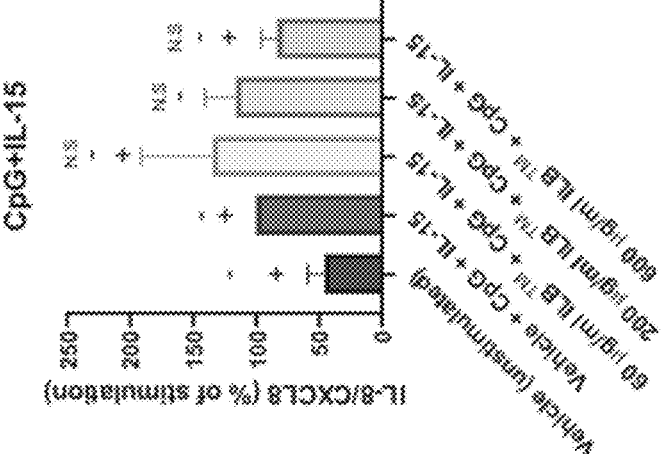

Dextran sulfate, or the pharmaceutically acceptable salt thereof, induced a reduction in the LPS and Cytostim stimulated secretion of IL-8 (FIGS. 4A and 4B).

IFNγ, also known as type II interferon, is a cytokine that is critical for innate and adaptive immunity against viral and intracellular bacterial infections. CD4 and CD8 T cells predominantly produce IFNγ upon antigen stimulation, and NK cells also produce IFNγ in the innate immune response. IFNγ is the primary cytokine used to define Th1 cells. Several studies indicated that IFNγ promoted the pro-inflammatory response during septic shock (Romero et al., The role of interferon-gamma in the pathogenesis of acute intra-abdominal sepsis, Journal of Leukocyte Biology, 88(4): 725-735 (2010)). IFNγ expression was enhanced persistently in patients who died of sepsis (Mera et al., (2011)).

Figure 3A:
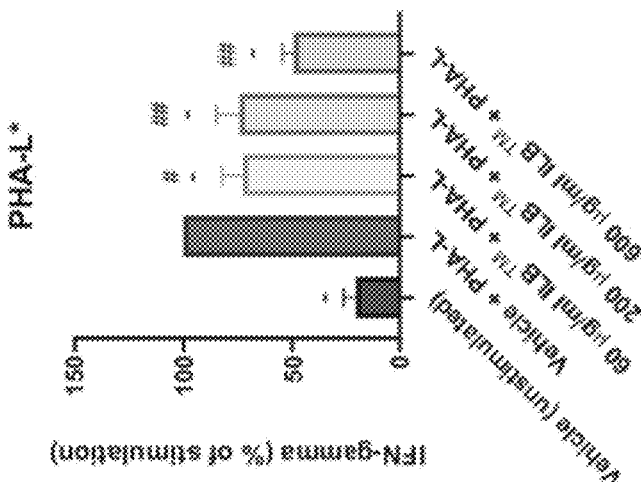
Figure 3A:
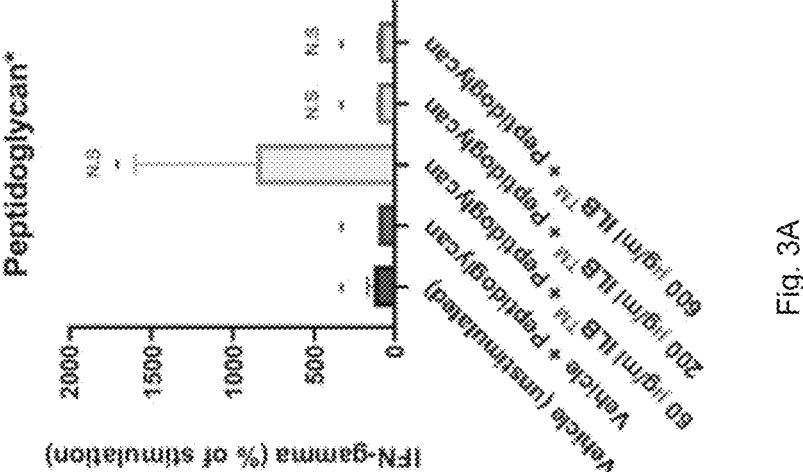
Figure 3A:
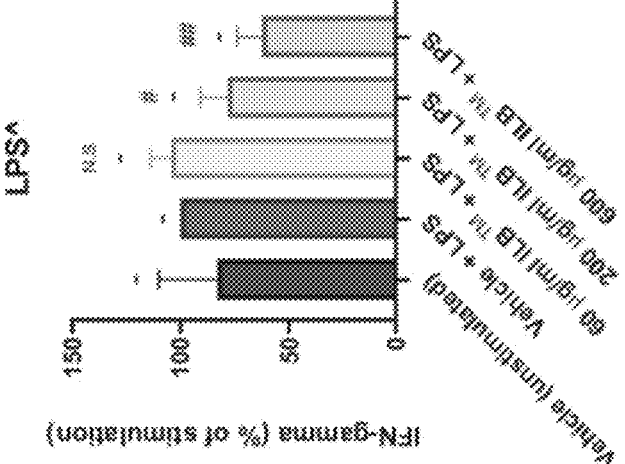

Dextran sulfate, or the pharmaceutically acceptable salt thereof, induced a reduction in the LPS, PHA-L and Cytostim stimulated secretion of IFNγ (FIGS. 3A and 3B).

TNFα, also referred to as cachexin or cachectin, stimulates the acute phase reaction involved in systemic inflammation. It has been documented that the plasma levels of TNFα increased significantly in patients with sepsis and in animal models (Mera et al., (2011)). TNFα has become the pro-inflammatory cytokine most well-studied in sepsis.

Figure 5A:
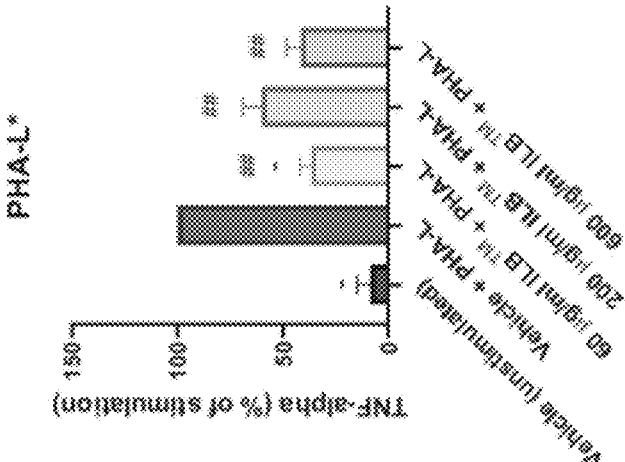
Figure 5A:
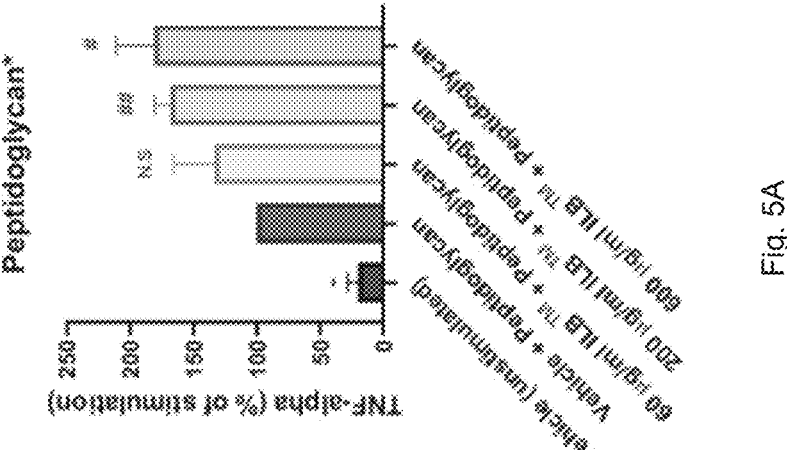
Figure 5A:
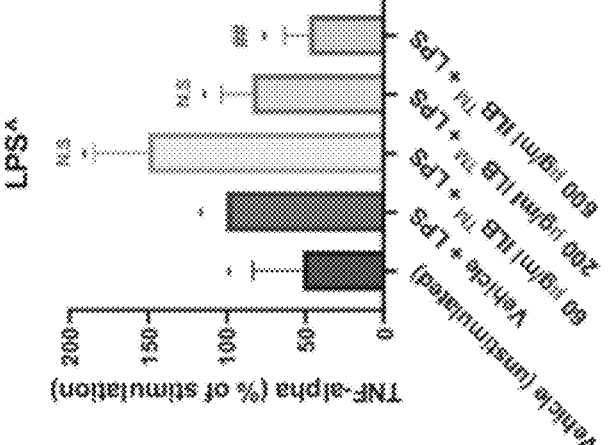

Dextran sulfate, or the pharmaceutically acceptable salt thereof, induced a reduction in the LPS, PHA-L and Cytostim stimulated secretion of TNFα (FIGS. 5A and 5B).

IL-10, also known as human cytokine synthesis inhibitory factor (CSIF), is a key cytokine in anti-inflammatory responses. CD4+Th2 cells, monocytes and B-cells produce IL-10. IL-10 powerfully inhibits the expression of Th1 cytokines, including both IL-2 and IFNγ. After binding to its high-affinity IL-10 receptor, IL-10 also suppresses the production of TNFα, IL-1, IL-6, IL-8, IL-12, GM-CSF, MIP-1α and MIP-2α in monocytes, macrophages, neutrophils and NK cells. IL-10 is one of the critical cytokines in the pathophysiology of sepsis. Measurement of serum cytokines in patients with severe sepsis indicated that the IL-10 level was significantly enhanced (Rau et al., Clinical manifestations but not cytokine profiles differentiate adult-onset still's disease and sepsis, The Journal of Rheumatology, 37(11): 2369-237641 (2010); Surbatovic et al., Immune cytokine response in combat casualties: Blast or explosive trauma with or without secondary sepsis, Military Medicine, 172(2): 190-195 (2007)). Increased IL-10 levels in serum were correlated with the sepsis score and death. A high IL-10-to-TNFα ratio was associated with death. Furthermore, persistent overproduction of IL-10 is the main risk factor for sepsis severity and fatal outcome (Gogos et al., Pro-versus anti-inflammatory cytokine profile in patients with severe sepsis: A marker for prognosis and future therapeutic options, *The Journal of Infectious Diseases*, 181(1):176-180 (2000)), suggesting that patients with sepsis are in profound immunosuppression.

Dextran sulfate, or the pharmaceutically acceptable salt thereof, induced a reduction in the LPS, PHA-L pokeweed and Cytostim stimulated secretion of IL-10 (FIGS. 7A and 7B).

In an embodiment, dextran sulfate, or the pharmaceutically acceptable salt thereof, is used in treatment of sepsis.

In a particular embodiment, dextran sulfate, or the pharmaceutically acceptable salt thereof, is used in treatment of severe sepsis.

In another particular embodiment, dextran sulfate, or the pharmaceutically acceptable salt thereof, is used in treatment of septic shock.

In another embodiment, dextran sulfate, or the pharmaceutically acceptable salt thereof, is used in treatment of hypercytokinemia.

In the following, reference to (average) molecular weight and sulfur content of dextran sulfate applies also to any pharmaceutically acceptable salt of dextran sulfate. Hence, the pharmaceutically acceptable salt of dextran sulfate preferably has the average molecular weight and sulfur content as discussed in the following embodiments.

Dextran sulfate outside of the preferred ranges of the embodiments are believed to have inferior effect and/or causing negative side effects to the cells or subject.

For instance, dextran sulfate of a molecular weight exceeding 10,000 Da (10 kDa) generally has a lower effect vs. side effect profile as compared to dextran sulfate having a lower average molecular weight. This means that the maximum dose of dextran sulfate that can be safely administered to a subject is lower for larger dextran sulfate molecules (>10,000 Da) as compared to dextran sulfate molecules having an average molecular weight within the preferred ranges. As a consequence, such larger dextran sulfate molecules are less appropriate in clinical uses when the dextran sulfate is to be administered to subjects in vivo.

Dextran sulfate is a sulfated polysaccharide and in particular a sulfated glucan, i.e., polysaccharide made of many glucose molecules. Average molecular weight as defined herein indicates that individual sulfated polysaccharides may have a molecular weight different from this average molecular weight but that the average molecular weight represents the mean molecular weight of the sulfated polysaccharides. This further implies that there will be a natural distribution of molecular weights around this average molecular weight for a dextran sulfate sample.

Average molecular weight, or more correctly weight average molecular weight ($M_w$), of dextran sulfate is typically determined using indirect methods such as gel exclusion/penetration chromatography, light scattering or viscosity. Determination of average molecular weight using such indirect methods will depend on a number of factors, including choice of column and eluent, flow rate, calibration procedures, etc.

Weight average molecular weight ($M_w$):

$$\frac{\sum M_i^2 N_i}{\sum M_i N_i},$$

typical for methods sensitive to molecular size rather than numerical value, e.g., light scattering and size exclusion chromatography (SEC) methods. If a normal distribution is assumed, then a same weight on each side of $M_w$, i.e., the total weight of dextran sulfate molecules in the sample having a molecular weight below $M_w$ is equal to the total weight of dextran sulfate molecules in the sample having a molecular weight above $M_w$. The parameter $N_i$ indicates the number of dextran sulfate molecules having a molecular weight of $M_i$ in a sample or batch.

In an embodiment, the dextran sulfate, or the pharmaceutically acceptable salt thereof, has a $M_w$ equal to or below 10,000 Da. In a particular embodiment, the dextran sulfate, or the pharmaceutically acceptable salt thereof, has a $M_w$ within an interval of from 2,000 Da to 10,000 Da.

In another embodiment, the dextran sulfate, or the pharmaceutically acceptable salt thereof, has a $M_w$ within an interval of from 2,500 Da to 10,000 Da, preferably within an interval of from 3,000 Da to 10,000 Da. In a particular embodiment, the dextran sulfate, or the pharmaceutically acceptable salt thereof, has a $M_w$ within an interval of from 3,500 Da to 9,500 Da, such as within an interval of from 3,500 Da to 8,000 Da.

In another particular embodiment, the dextran sulfate, or the pharmaceutically acceptable salt thereof, has a $M_w$ within an interval of from 4,500 Da to 7,500 Da, such as within an interval of from 4,500 Da and 6,500 Da or within an interval of from 4,500 Da and 5,500 Da.

Thus, in some embodiments, the dextran sulfate, or the pharmaceutically acceptable salt thereof, has a $M_w$ equal to or below 10,000 Da, equal to or below 9,500 Da, equal to or below 9,000 Da, equal to or below 8,500 Da, equal to or below 8,000 Da, equal to or below 7,500 Da, equal to or below 7,000 Da, equal to or below 6,500 Da, equal to or below 6,000 Da, or equal to or below 5,500 Da.

In some embodiments, the dextran sulfate, or the pharmaceutically acceptable salt thereof, has a $M_w$ equal to or above 1,000 Da, equal to or above 1,500 Da, equal to or above 2,000 Da, equal to or above 2,500 Da, equal to or above 3,000 Da, equal to or above 3,500 Da, equal to or above 4,000 Da. or equal to or above 4,500 Da. Any of these embodiments may be combined with any of the above presented embodiments defining upper limits of the $M_w$, such combined with the upper limit of equal to or below 10,000 Da.

In a particular embodiment, the $M_w$ of dextran sulfate, or the pharmaceutically acceptable salt thereof, as presented above is average $M_w$, and preferably determined by gel exclusion/penetration chromatography, size exclusion chromatography, light scattering or viscosity-based methods.

Number average molecular weight ($M_n$):

$$\frac{\sum M_i N_i}{\sum N_i},$$

typically derived by end group assays, e.g., nuclear magnetic resonance (NMR) spectroscopy or chromatography. If a normal distribution is assumed, then a same number of dextran sulfate molecules can be found on each side of $M_n$, i.e., the number of dextran sulfate molecules in the sample having a molecular weight below $M_n$ is equal to the number of dextran sulfate molecules in the sample having a molecular weight above $M_n$.

In an embodiment, the dextran sulfate, or the pharmaceutically acceptable salt thereof, has a $M_n$ as measured by NMR spectroscopy within an interval of from 1,850 to 3,500 Da.

In a particular embodiment, the dextran sulfate, or the pharmaceutically acceptable salt thereof, has a $M_n$ as measured by NMR spectroscopy within an interval of from 1,850 Da to 2,500 Da, preferably within an interval of from 1,850 Da to 2,300 Da, such as within an interval of from 1,850 Da to 2,000 Da.

Thus, in some embodiments, the dextran sulfate, or the pharmaceutically acceptable salt thereof, has a $M_n$ equal to or below 3,500 Da, equal to or below 3,250 Da, equal to or below 3,000 Da, equal to or below 2,750 Da, equal to or below 2,500 Da, equal to or below 2,250 Da, or equal to or below 2,000 Da. In addition, the dextran sulfate, or the pharmaceutically acceptable salt thereof, has a $M_n$ equal to or above 1,850 Da.

In an embodiment, the dextran sulfate, or the pharmaceutically acceptable salt thereof, has an average sulfate number per glucose unit within an interval of from 2.5 to 3.0.

In a particular embodiment, the dextran sulfate, or the pharmaceutically acceptable salt thereof, has an average sulfate number per glucose unit within an interval of from 2.5 to 2.8, preferably within an interval of from 2.6 to 2.7.

In an embodiment, the dextran sulfate, or the pharmaceutically acceptable salt thereof, has an average number of glucose units within an interval of from 4.0 to 6.0.

In a particular embodiment, the dextran sulfate, or the pharmaceutically acceptable salt thereof, has an average number of glucose units within an interval of from 4.5 to 5.5, preferably within an interval of from 5.0 to 5.2.

In an embodiment, the dextran sulfate, or the pharmaceutically acceptable salt thereof, has a $M_n$ as measured by NMR spectroscopy within an interval of from 1,850 to 3,500 Da, an average sulfate number per glucose unit within an interval of from 2.5 to 3.0, and an average sulfation of C2 position in the glucose units of the dextran sulfate is at least 90%.

In an embodiment, the dextran sulfate has an average number of glucose units of about 5.1, an average sulfate number per glucose unit within an interval of from 2.6 to 2.7 and a $M_n$ within an interval of from 1,850 Da and 2,000 Da.

In an embodiment, the pharmaceutically acceptable salt of dextran sulfate is a sodium salt of dextran sulfate. In a particular embodiment, the sodium salt of dextran sulfate has an average number of glucose units of about 5.1, an average sulfate number per glucose unit within an interval of from 2.6 to 2.7 and a Mo including the $Na^+$ counter ion within an interval of from 2,100 Da to 2,300 Da.

In an embodiment, the dextran sulfate has an average number of glucose units of 5.1, an average sulfate number per glucose unit of 2.7, an average $M_n$ without $Na^+$ as measured by NMR spectroscopy of about 1,900-1,950 Da and an average $M_n$ with $Na^+$ as measured by NMR spectroscopy of about 2,200-2,250 Da.

The dextran sulfate according to the embodiments can be provided as a pharmaceutically acceptable salt of dextran sulfate, such as a sodium or potassium salt.

In an embodiment, a dextran sulfate, or a pharmaceutically acceptable salt thereof, as disclosed in WO 2016/076780 is used.

The subject is preferably a mammalian subject, more preferably a primate and in particular a human subject. The dextran sulfate, or the pharmaceutically acceptable salt thereof, can, however, be used also in veterinary applications. Non-limiting example of animal subjects include primate, cat, dog, pig, horse, mouse, rat.

The dextran sulfate, or the pharmaceutically acceptable salt thereof, is preferably administered by injection to the subject and in particular by intravenous (i.v.) injection, subcutaneous (s.c.) injection or (i.p.) intraperitoneal injection, preferably i.v. or s.c. injection. Other parenteral administration routes that can be used include intramuscular and intraarticular injection. Injection of the dextran sulfate, or the pharmaceutically acceptable derivative thereof, could alternatively, or in addition, take place directly in, for instance, a tissue or organ or other site in the subject body, at which the target effects are to take place.

The dextran sulfate, or the pharmaceutically acceptable salt thereof, of the embodiments is preferably formulated as an aqueous injection solution with a selected solvent or excipient. The solvent is advantageously an aqueous solvent and in particular a buffer solution. A non-limiting example of such a buffer solution is a citric acid buffer, such as citric acid monohydrate (CAM) buffer, or a phosphate buffer. For instance, dextran sulfate of the embodiments can be dissolved in saline, such as 0.9% NaCl saline, and then optionally buffered with 75 mM CAM and adjusting the pH to about 5.9 using sodium hydroxide. Also, non-buffered solutions are possible, including aqueous injection solutions, such as saline, i.e., NaCl (aq). Furthermore, other buffer systems than CAM could be used if a buffered solution are desired.

The embodiments are not limited to injections and other administration routes can alternatively be used including orally, nasally, bucally, rectally, dermally, tracheally, bronchially, or topically. The active compound, dextran sulfate, is then formulated with a suitable excipient or carrier that is selected based on the particular administration route.

Suitable dose ranges for the dextran sulfate, or the pharmaceutically acceptable salt thereof, may vary according to the application, such as in vitro versus in vivo, the size and weight of the subject, the severity of the sepsis condition for which the subject is treated, and other considerations. In particular for human subjects, a possible dosage range could be from 1 µg/kg to 100 mg/kg of body weight, preferably from 10 µg/kg to 50 mg/kg of body weight.

In preferred embodiments, the dextran sulfate, or the pharmaceutically acceptable salt thereof, is formulated to be administered at a dosage in a range from 0.05 to 50 mg/kg of body weight of the subject, preferably from 0.05 or 0.1 to 40 mg/kg of body weight of the subject, and more preferably from 0.05 or 0.1 to 30 mg/kg, or 0.1 to 25 mg/kg or from 0.1 to 15 mg/kg or 0.1 to 10 mg/kg body weight of the subject. Preferred dosages are selected in a range from 0.25 to 5 mg/kg, preferably 0.5 to 2.5 mg/kg, and more preferably 0.75 to 2 mg/kg body weight of the subject.

The dextran sulfate, or the pharmaceutically acceptable derivative thereof, can be administered at a single administration occasion, such as in the form of a single bolus injection. This bolus dose can be injected quite quickly to the subject but is advantageously infused over time so that the dextran sulfate solution is infused over a few minutes of time to the patient, such as during 5 to 10 minutes.

Alternatively, the dextran sulfate, or the pharmaceutically acceptable salt thereof, can be administered at multiple, i.e., at least two, occasions during a treatment period.

The dextran sulfate, or the pharmaceutically acceptable salt thereof, can be administered together with other active agents, either sequentially, simultaneously or in the form of a composition comprising the dextran sulfate, or the pharmaceutically acceptable salt thereof, and at least one other active agent. The at least one active agent can be selected among any agent useful in treatment of sepsis.

The invention also relates to the use of dextran sulfate, or a pharmaceutically acceptable salt thereof, in the manufacture of a medicament for treatment of sepsis and/or hypercytokinemia.

The invention also defines a method for treating sepsis and/or hypercytokinemia. The method comprises administering dextran sulfate, or a pharmaceutically acceptable salt thereof, to a subject suffering from sepsis and/or hypercytokinemia. In a particular embodiment, dextran sulfate, or the pharmaceutically acceptable salt thereof, is administered to a subject suffering from an infection or an infectious disease, and in particular such an infection or infectious disease that may cause sepsis and/or hypercytokinemia in the subject.

The term "treatment" and "treating" as used herein means the management and care of a patient for the purpose of combating sepsis and/or hypercytokinemia. The term is intended to include the full spectrum of treatments for sepsis and/or hypercytokinemia, such as administration of dextran sulfate, or the pharmaceutically acceptable salt thereof, to alleviate the symptoms or complications, to delay the progression of the disease, to alleviate or relief the symptoms and complications, and/or to cure or eliminate the disease as well as to prevent sepsis and/or hypercytokinemia, wherein prevention is to be understood as the management and care of a patient for the purpose of combating sepsis and/or hypercytokinemia and includes the administration of dextran sulfate, or the pharmaceutically acceptable salt thereof, to prevent the onset of the symptoms or complications. The treatment may either be performed in an acute or in a chronic way. Treatment as used herein also encompasses prophylaxis or preventing sepsis and/or hypercytokinemia and inhibition of sepsis and/or hypercytokinemia, including inhibition of the symptoms of sepsis and/or hypercytokinemia.

The term "a therapeutically effective amount" of dextran sulfate, or the pharmaceutically salt thereof, for as used herein means an amount sufficient to cure, inhibit, alleviate or partially arrest the clinical manifestations of sepsis and/or hypercytokinemia and its complications. An amount adequate to accomplish this is defined as "therapeutically effective amount". Effective amounts for each purpose will depend on the severity of the disease as well as the weight and general state of the patient. It will be understood that determining an appropriate dosage may be achieved using routine experimentation, by constructing a matrix of values and testing different points in the matrix, which is all within the ordinary skills of a trained physician or veterinary.

EXAMPLES

Example 1

This Example investigated the ability of low molecular weight dextran sulfate (LMW-DS) to impact stimulated release of IL-6 from human peripheral blood mononuclear cells (PBMCs) in vitro.

Human PBMCs can be stimulated in vitro by a variety of agents that will activate directly and indirectly various cell subsets. Monitoring cytokine release allows the potential impact of drugs to be investigated to predict action in patients. IL-6 is an archetypical pro-inflammatory cytokine that has been shown to be associated with numerous pathologies including sepsis.

Materials & Methods

PBMCs were isolated from healthy donors through Ficoll-Paque PLUS (GE Healthcare; 11778538) density centrifugation. PBMC were cultured at $2 \times 10^5$ cells/well in the absence (unstimulated phosphate-buffered saline (PBS) vehicle controls) or presence of stimulation (lipopolysaccharide (LPS), peptidoglycan, pokeweed mitogen, phytohemagglutinin-L (PHA-L), CpG+IL-15, or Cytostim) in the absence (vehicle) or presence of LMW-DS (ILB®, Tikomed AB, Viken, Sweden, WO 2016/076780) at three concentrations; 60 µg/ml, 200 µg/ml and 600 µg/ml for 24 hours at 37° C., 5% $CO_2$. Following centrifugation, cell culture supernatants were removed and stored at −20° C. awaiting analysis for IL-6 by ELISA. Levels of IL-6 were quantified in the supernatant by ELISA (R&D systems; DY206) according to manufacturer's instructions.

Results

Historical internal data guided selection of stimulus concentration to use sub-maximal concentrations of LPS, peptidoglycan, pokeweed mitogen, PHA-L, CpG+IL-15 and Cytostim. With the PBMC mix, all the stimulations increased IL-6 release into the cell culture supernatant. With promising results generated from the cells from the first six donors with respect to the impact of LMW-DS upon LPS stimulation, it was decided to extend the LPS studies in a further six donors. Furthermore, relative to unstimulated PBMCs, the original selected concentrations of CpG+IL-15 and Cytostim gave relatively low increases in IL-6 release. Therefore, in the cells from the additional six donors, higher concentrations of CpG+IL-15 and Cytostim were investigated. These higher concentrations evoked a greater increase in IL-6 release relative to the unstimulated cells.

LPS

LPS is a toll-like receptor (TLR) 4 agonist. In a human PBMC mix, the main cell type activated directly by LPS is monocytes, which express TLR4. Monocytes are part of the innate immune system. These myeloid cells can also be used to model responses to other myeloid cells, such as macrophages and microglia. In the present Example, LPS evoked a substantial increase in the release of IL-6 into the cell culture supernatant (FIG. 1A). LMW-DS caused a concentration dependent and statistically significant reduction in IL-6 concentrations (FIG. 1A). This indicates that LMW-DS displays potential to reduce the pro-inflammatory consequences of IL-6 following TLR4 activation of monocytes.

Peptidoglycan

Peptidoglycan is a TLR2 agonist, which in a PBMC mix is expressed predominantly by monocytes and B lymphocytes. The latter are a component of the acquired immune system best known for displaying an integral role in the generation of specific antibodies to antigens. Peptidoglycan evoked a substantial increase in the release of IL-6 into the cell culture supernatant but overall from experiments with cells from six donors there was little evidence of LMW-DS, even at the highest concentration tested, of causing a general reduction in IL-6 release (FIG. 1B).

Pokeweed Mitogen

Figure 1D:
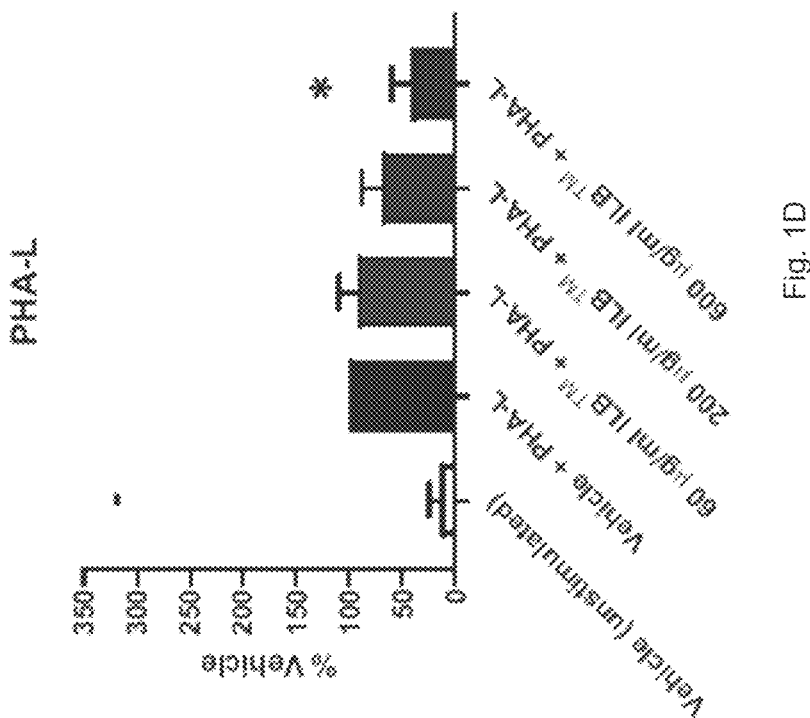
Figure 1C:
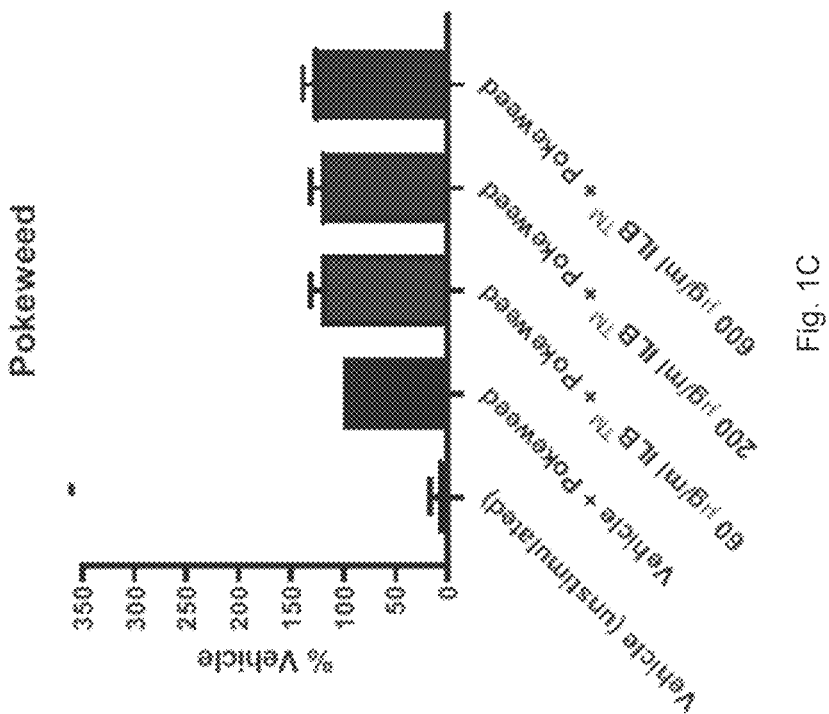

Pokeweed mitogen is a lectin purified from *Phytolacca americana*. It evokes a T lymphocyte-dependent activation of B lymphocytes. In the present studies, pokeweed mitogen evoked a large increase in IL-6 release by the PBMC mix but this release was not impacted generally by LMW-DS (FIG. 1C).

PHA-L

PHA-L is the L-type subunit lectin from *Phaseolus vulgaris* (red kidney beans), which crosslinks T lymphocyte surface receptors resulting in their activation. PHA-L induced a relatively modest increase in IL-6 release from the PBMC mix and this was inhibited significantly in a concentration-dependent manner by LMW-DS (FIG. 1D).

CpG+IL-15

Figure 1F:
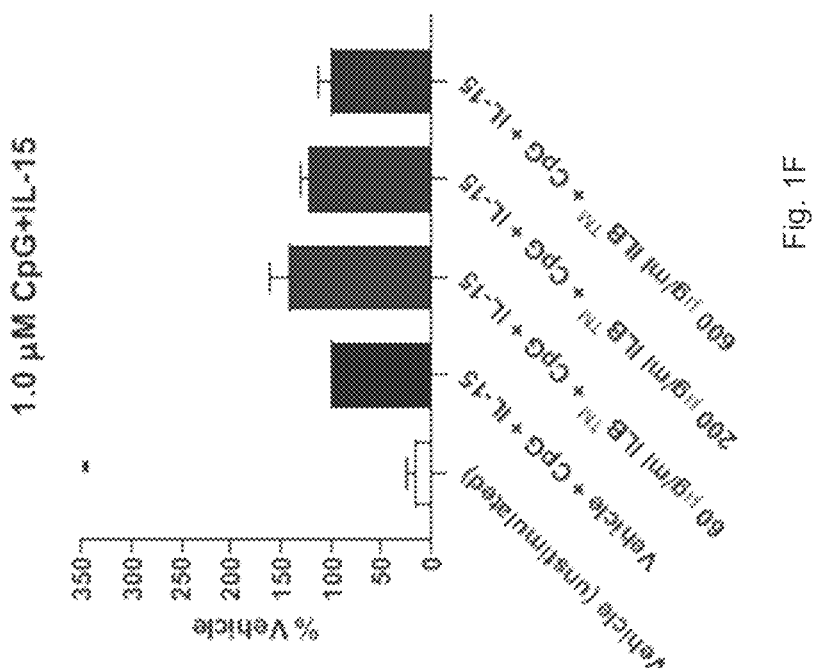
Figure 1E:
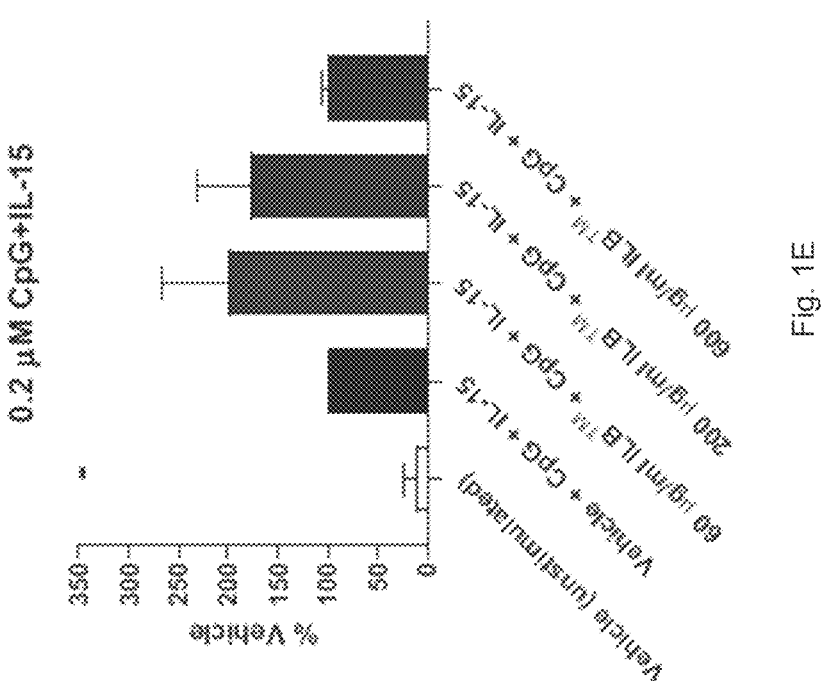

CpG-oligodeoxynucleotides (ODN) are short single-stranded deoxyribonucleic acid (DNA) molecules that activate TLR9, which within a PBMC mix is expressed mainly by monocytes and B cells. IL-15 synergizes with CpG in the stimulation of B lymphocytes. Unlike pokeweed mitogen, CpG+IL-15 activates B lymphocytes directly, i.e., is T lymphocyte independent. In the first round of experiments with PBMC from six donors, the concentration of CpG-ODN+IL-15 selected evoked only small increases in IL-6 release into the cell culture supernatant. Whilst this relatively low level of IL-6 release was not generally impacted by LMW-DS (FIG. 1E), with the additional experiments performed with extra donors to increase the n number for the LPS stimulation, these same extra donors were subject to application of a higher concentration of CpG+IL-15 in an attempt to evoke a more robust release of IL-6 above that evident from the unstimulated cells; whilst this was achieved there was still no general impact of LMW-DS (FIG. 1F).

Cytostim

Figure 1H:
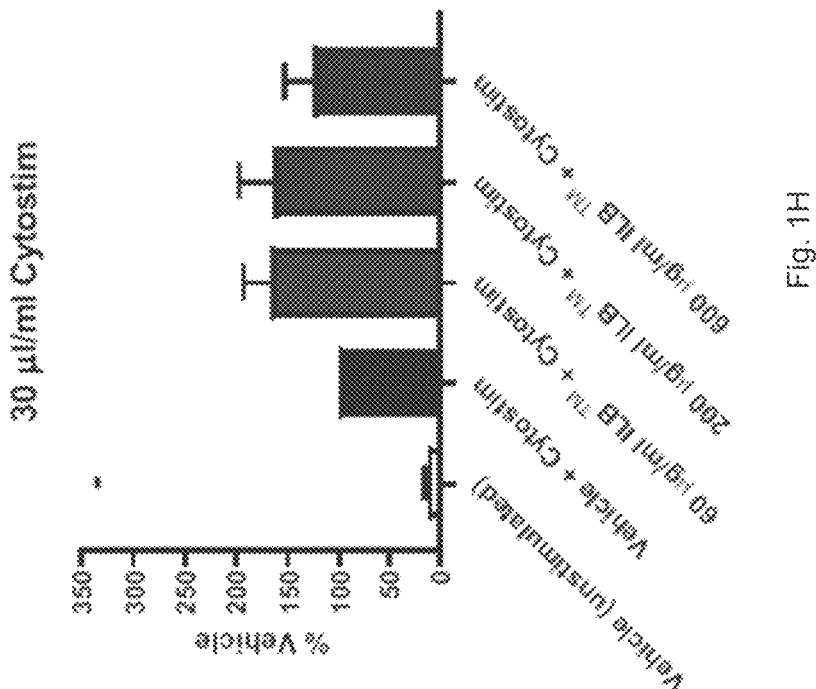
Figure 1G:
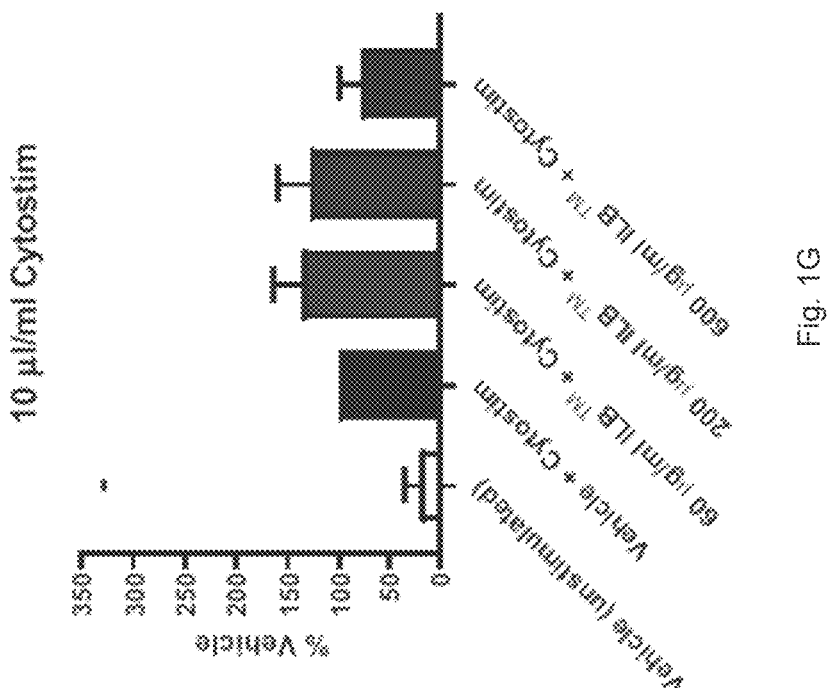

Cytostim is an antibody-based activator of T lymphocytes. It binds to the T cell receptor (TCR) and cross links this to the major histocompatibility complex (MHC) molecule of an antigen-presenting cell. Thus, Cytostim stimulates both cluster of differentiation 4 (CD4) and CD8 T lymphocytes. In the present Example, the first round of experiments with PBMC from six donors used a concentration of Cytostim that led only to small relatively small increases in IL-6 release into the cell culture supernatant, which was not generally impacted by LMW-DS (FIG. 1G). PBMC from these same extra donors were investigated with a higher concentration of Cytostim to evoke a greater release of IL-6 relative to the IL-6 release from the unstimulated cells yet there was still no general impact of LMW-DS (FIG. 1H).

Whilst all the stimuli investigated in the present Example were able to increase IL-6 release from cells in a PBMC mix, the targeted action of LMW-DS (to LPS and PHA-L) upon IL-6 release suggests a refined mode of action rather than a general ability to reduce IL-6 release.

Example 2

Monocytes are circulating innate immune cells that are a key component of the immune system. In addition, as they are readily accessible, they can be used as cells to model other myeloid cells that are less easy to access such as macrophages and microglia.

Like various myeloid cells, monocytes can be activated via Toll-Like receptor (TLR) agonists, like the TLR2 and the TLR4 receptor agonists, peptidoglycan and lipopolysaccharide (LPS), respectively. Activation can be monitored by the expression of activation markers (by flow cytometry) and/or secretion of cytokines, such as the pro-inflammatory cytokine interleukin-6 (IL-6). In Example 1, LMW-DS reduced the secretion of IL-6 in a human peripheral blood mononuclear cell (PBMC) preparation in response to LPS stimulation. However, the multiplicity of cell types in PBMC mix prevents interpretation of the precise cell type(s) mediating this response. The present study investigated the ability of LMW-DS to modify LPS-stimulated IL-6 release from human purified monocytes in an attempt to identify a precise cellular target for LMW-DS. IL-6 is an archetypical pro-inflammatory cytokine that is associated with numerous pathologies including sepsis.

Materials & Methods

Peripheral blood mononuclear cells (PBMC) were isolated from healthy donors through Ficoll-Paque PLUS (GE Healthcare; 11778538) density centrifugation. Monocytes were purified using the EasySep™ human monocyte enrichment kit (StemCell) that purifies monocytes 'untouched' to maintain their phenotype.

Monocytes were cultured in the absence (unstimulated PBS vehicle controls) or presence of stimulation (LPS or peptidoglycan) in the absence (vehicle) or presence of LMW-DS (ILB®, Tikomed AB, Viken, Sweden, WO 2016/076780; three concentrations: 600 µg/ml, 200 µg/ml and 60

μg/ml), heparin (2.0, 6.0 or 20 μg/ml; equivalent to 0.406, 1.218 and 4.06 units/ml; Sigma Aldrich) or dexamethasone (3.0 μM; Sigma Aldrich) for 24 hours at 37° C., 5% $CO_2$. Following centrifugation, cell culture supernatants were removed and stored at –20° C. awaiting analysis for IL-6 by ELISA. Levels of IL-6 were quantified in the supernatant by ELISA (R&D systems) according to manufacturer's instructions.

Results

Historical internal data guided selection of the stimulus concentration and the use of sub-maximal concentrations of LPS and peptidoglycan. These also corresponded to the same concentrations of LPS and peptidoglycan used in Example 1 when a human PBMC mix was used as the source of IL-6.

The TLR2 agonist peptidoglycan and the TLR4 agonist LPS evoked release of IL-6 into the cell culture supernatant from the human purified monocytes (FIG. 2).

Average results with monocytes from ten healthy donors demonstrated a concentration dependent statistically significant inhibition of LPS-stimulated IL-6 release into the cell culture supernatant by LMW-DS (FIG. 2A), whereas heparin evoked a concentration dependent statistically significant enhancement of LPS-stimulated IL-6 release into the cell culture supernatant (FIG. 2C). As expected, the glucocorticoid steroid dexamethasone inhibited the LPS-stimulated IL-6 release into the cell culture supernatant in a statistically significant manner (FIG. 2B).

Average results with monocytes from ten healthy donors demonstrated a concentration dependent statistically significant increase of peptidoglycan-stimulated IL-6 release into the cell culture supernatant by LMW-DS (FIG. 2D). This enhancement was mirrored to some extent by heparin although the trend did not reach statistical significance (FIG. 2F). As expected, the presence of dexamethasone resulted in a statistically significant inhibition of peptidoglycan-stimulated IL-6 release into the cell culture supernatant (FIG. 2E).

Monocytes are part of the innate immune system. These myeloid cells can also be used to model responses to other myeloid cells such as macrophages and microglia. In the present Example, the clear and substantial impact of LMW-DS to inhibit the LPS evoked increase in the release of IL-6 from purified monocytes provides strong evidence that these cells represent a target for LMW-DS.

Example 3

Activation of the immune response in diseased or infected tissues is reflected by changes in the phenotypic balance of peripheral blood mononuclear cells (PBMC). Hence, assessing the impact of drugs upon components of the adaptive and innate immune systems may reveal mechanistic cellular pathways to better understand clinical changes associated with the investigational therapy as well as potentially identifying cellular and/or molecular biomarkers predicting therapeutic efficacy for different pathologies.

Human PBMCs can be stimulated in vitro by a variety of agents that will activate directly and indirectly various cell subsets and mimic immune responses associated with compromised tissues. Monitoring cytokine release from PBMC allows the potential impact of drugs to be investigated and to predict drug action in specific patient aetiologies.

Materials & Methods

Example 1 investigated the ability of LMW-DS to modify the secretion of IL-6 from human PBMCs arising from the use of various stimuli. The present study performed a broader analysis of the cell culture supernatants arising from Example 1. Thus, peripheral blood mononuclear cells (PBMC) were isolated from healthy donors through Ficoll-Paque PLUS density centrifugation. The PBMC were cultured at $2\times10^5$ cells/well in the absence (unstimulated PBS vehicle controls) or presence of stimulation (LPS, peptidoglycan, pokeweed mitogen, PHA-L, CpG+IL-15, or Cytostim) in the absence (vehicle) or presence of LMW-DS (ILB®, Tikomed AB, Viken, Sweden, WO 2016/076780; three concentrations; 600 μg/ml, 200 μg/ml and 60 μg/ml) for 24 hours at 37° C., 5% $CO_2$.

Accordingly, the treatments were as follows for each PBMC donor:
  i. Vehicle
  ii. Simulation
  iii. Stimulation+LMW-DS (60 μg/ml)
  iv. Stimulation+LMW-DS (200 μg/ml)
  v. Stimulation+LMW-DS (600 μg/ml)
  with each assessed in triplicate such that the total numbers of samples were:
  1. LPS; 165 samples (from 11 donors)
  2. Peptidoglycan from *Bacillus subtilis;* 90 samples (from 6 donors)
  3. PHA-L; 90 samples (from 6 donors)
  4. 0.2 μM CpG+IL-15; 90 samples (from 6 donors)
  5. 1.0 μM CpG+IL-15; 90 samples (from 6 donors)
  6. Pokeweed mitogen; 90 samples (from 6 donors)
  7. 10 μl/ml Cytostim; 90 samples (from 6 donors)
  8. 30 μl/ml Cytostim; 90 samples (from 6 donors)
  Total number of supernatant samples from all stimulations (all cell types)=795

Following treatment, cell culture supernatants were removed, centrifuged and stored at –20° C. before thawing for multiplex analysis of various cytokines using the 5-plex human magnetic Luminex assay from R&D systems (Cat. No. LXSAHM-05). Luminex analysis was carried out exactly following manufacturer's protocols.

Results

Historical internal data guided selection of stimulus concentration to use sub-maximal concentrations of LPS, peptidoglycan, pokeweed mitogen, PHA-L, CpG+IL-15 and Cytostim; use of sub-maximal concentrations of stimulus tends to allow both increases and decreases in modulation to be identified when present. With the PBMC mix, all the stimulations increased release of cytokines into the cell culture supernatant although some stimuli were more effective than others (FIGS. 3A-7B).

LPS

LPS (lipopolysaccharide) is a toll-like receptor (TLR) 4 agonist. In a human PBMC mix, the main cell type activated directly by LPS is monocytes, which express TLR4. Monocytes are part of the innate immune system. These myeloid cells can also be used to model responses to other myeloid cells such as macrophages and microglia. In the present studies, when evaluating the effect of LPS, there was a modest increase in the secretion of IFNγ, TNFα, IL-1β and IL-10 but a substantial increase in IL-8 secretion (FIGS. 3A-7B). LMW-DS was responsible for a concentration dependent but small reduction in IFNγ and IL-10 (FIGS. 3A, 3B, 7A and 7B), and the presence of the highest concentration of LMW-DS resulted in a modest reduction in the stimulated secretion of IL-1β, IL-8 and TNFα (FIGS. 4A-6B).

Peptidoglycan

Peptidoglycan is a TLR2 agonist, which in a PBMC mix is expressed predominantly by monocytes and B lymphocytes. The latter are a component of the acquired immune system best known for displaying an integral role in the generation of specific antibodies to antigens. Peptidoglycan evoked an increase in the release of IL-1β, IL-8 and TNFα into the cell culture supernatant but overall, from examining the results from all the donors, there was little evidence of LMW-DS, even at the highest concentration tested, of causing a general reduction in cytokine release although there were associated increases in IL-1β and TNFα secretion (FIGS. 4A-6B).

PHA-L

PHA-L (phytohemagglutinin-L) is the L-type subunit lectin from *Phaseolus vulgaris* (red kidney beans), which crosslinks T lymphocyte surface receptors resulting in their activation. In the PBMC mix, PHA-L induced increases in IFNγ, IL-8, IL-10 and TNFα and a modest increase overall in IL-1β (FIGS. 4A-7B). LMW-DS resulted in small decreases in stimulated release of IFNγ, IL-8, TNFα but not IL-1β (FIGS. 4A-6B). By contrast, LMW-DS resulted in a large, concentration dependent decrease in IL-10 secretion (FIGS. 7A and 7B).

Pokeweed Mitogen

Pokeweed mitogen is a lectin purified from *Phytolacca americana*. It evokes a T lymphocyte-dependent activation of B lymphocytes. In the present studies, pokeweed mitogen evoked robust increases in the secretion of IFNγ, IL-1β, IL-8, IL-10 and TNFα by the PBMC mix (FIGS. 4A-7B), but this release was not impacted generally by LMW-DS except for a concentration-dependent decrease in IL-10 secretion (FIGS. 7A and 7B).

CpG+IL-15

CpG-ODNs are short single-stranded DNA molecules that activate TLR9, which within a PBMC mix is expressed mainly by monocytes and B cells. IL-15 synergizes with CpG in the stimulation of B lymphocytes. Unlike pokeweed mitogen, CpG+IL-15 activates B lymphocytes directly, i.e., is T lymphocyte independent. In the present studies, there was only robust evidence for this stimulation to increase secretion of IL-8. Overall, LMW-DS displayed little impact on this response in these experiments (FIGS. 4A-7B).

Cytostim

Cytostim is an antibody-based activator of T lymphocytes. It binds to the T cell receptor (TCR) and cross links this to the major histocompatibility complex (MHC) molecule of an antigen-presenting cell. Thus, Cytostim stimulates both CD4 and CD8 T lymphocytes. Overall, Cytostim evoked an increase in the secretion of IFNγ, IL-1β, IL-8, IL-10 and TNFα (FIGS. 4A-7B), with small reductions associated with the presence of LMW-DS except for IL-10 secretion where there was a concentration dependent large reduction evident in the presence of LMW-DS (FIGS. 7A and 7B).

Overall, the data support a potential action of LMW-DS to benefit patients with sepsis. Sepsis following infection is considered a dysregulated immune response resulting in organ dysfunction. Sepsis is responsible for major morbidity, mortality and healthcare expenditure. Worldwide there are an estimated 31.5 million cases of sepsis per year, and in the UK 46,000 deaths per year with an estimated cost to the NHS of £1.5-2.0 billion per year.

During sepsis, in response to an infection, excessive production of inflammatory cytokines (cytokine storm) may cause septic shock. Several of the cytokines modulated by LMW-DS are both elevated and considered to contribute to the pathogenesis of sepsis. For example, IFNγ, IL-1β, IL-6, IL-8 and TNFα exhibit a persistent increase in non-survivors (Mera et al., (2011)). TNFα and IL-1β are considered to play major roles in sepsis and act on cells, such as macrophages, where they amplify inflammatory cascades to increase release of other pro-inflammatory cytokines as well as reactive oxygen and nitrogen species, and endothelial cells, where they mediate inflammation-induced activation of coagulation (Schulte et al., Cytokines in sepsis: potent immunoregulators and potential therapeutic targets—an updated view, *Mediators of Inflammation*, 2013: 165974 (2013)). Additional roles of TNFα include promoting neutrophil extravasation through action on endothelial cells and it has been demonstrated that blockade of TNFα with monoclonal antibodies may also improve survival in patients with severe sepsis. IL-6 can enhance the activation of T cells, B cells and the coagulation system, and levels of IL-6 correlate with the clinical severity of sepsis (Schulte et al., (2013)). Knockout of IL-6 reduces lung damage in a mouse model of acute lung injury. IL-8 acts to potently attract and activate neutrophils, and levels correlate with the severity of sepsis (Kraft et al., Predictive value of IL-8 for sepsis and severe infections after burn injury, Shock, 43(3): 222-227 (2015)). In addition to pathological roles in sepsis, cytokines may play host protective roles in host defense and immune regulation, and so despite the promise in targeting them described above, the role of cytokines in sepsis remains a 'double-edged sword' (Chaudhry et al., Role of cytokines as a double-edged sword in sepsis, In Vivo, 27(6): 669-684 (2013)).

One challenge in sepsis is how to target elements of a response without generating prolonged immunosuppression. Whilst benefits of neutralizing TNFα in sepsis have been demonstrated, monoclonal antibodies, with their long half-life, e.g., infliximab, adalimumab and certolizumab have half-life values of around 14 days, raise challenges in the timing and route of administration. Agents that target multiple cytokines, in a specific phase of the disease with a relatively short duration of action, like LMW-DS, could therefore bring potential additional clinical benefit to patients with sepsis.

Example 4

Materials & Methods

Serum samples were taken from Motor Neuron Disease (MND)/Amyotrophic Lateral Sclerosis (ALS) patients in a clinical trial (EudraCT Number: 2018-000668-28) prior to and 5, 10 and 24 weeks following treatment with LMW-DS (ILB®, Tikomed AB, Viken, Sweden, WO 2016/076780). Frozen serum samples were thawed and quantified for IL-6 using the Luminex assay system (Bio-Plex 200 system with Bio-Plex Manager software) according to manufacturer's instructions. After an initial screening visit, patients had weekly dosing of a single LMW-DS (ILB®, Tikomed AB, Viken, Sweden, WO 2016/076780) injection of 1.0 mg/kg body weight in saline into the subcutaneous fat of the lower abdomen with a maximum of 1.5 mL at each injection site.

Statistical analysis was performed using the non-parametric Mann-Whitney U test with $p < 0.05$ considered significant.

Results

Figure 8:
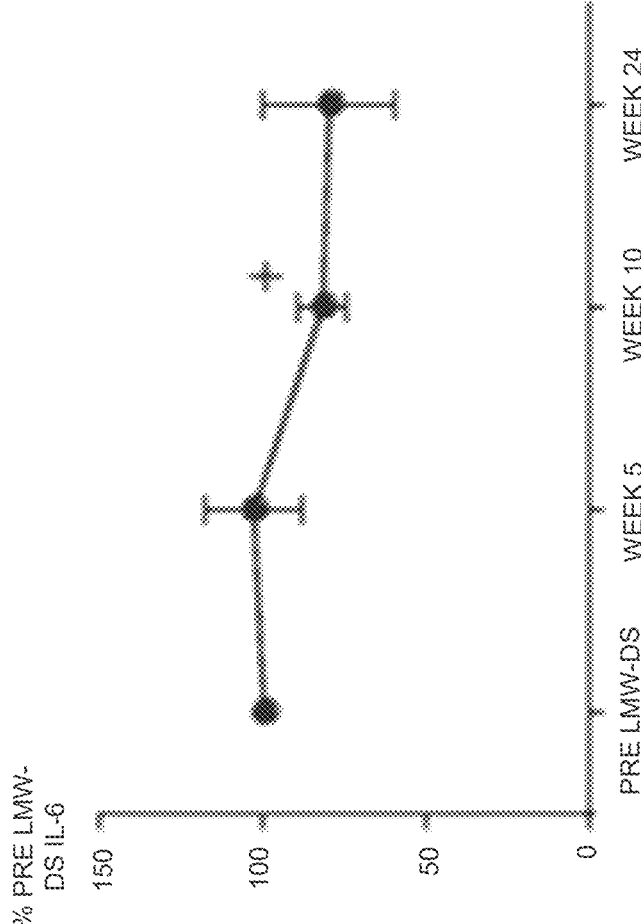
FIG. 8 Serum levels of IL-6 following administration of LMW-DS (weeks 5, 10 and 24) as a % of Pre-LMW-DS levels. Data presented as percentage of cytokine levels pre-LMW-DS treatment. Data presented as mean±SEM of 8 patients. +P<0.05.

FIG. 8 illustrates serum levels of various IL-6 assayed by Luminex assay system in the serum samples collected from each 8 ALS patients. To allow comparison across the patient cohort, the % change in the concentration in the blood of IL-6 subsequent to initiating LMW-DS administration to patients after 5, 10 and 24 weeks were evaluated. The analysis demonstrated a statistically significant decrease in IL-6 levels measured at 10 weeks of treatment.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

The invention claimed is:

1. A method for treating sepsis comprising administering dextran sulfate, or a pharmaceutically acceptable salt thereof, having a number average molecular weight (Mn) as measured by nuclear magnetic resonance (NMR) spectroscopy within a range of from 1850 to 3500 Da and an average sulfate number per glucose unit within a range of from 2.5 to 3.0 to a subject suffering from sepsis.

2. The method according to claim 1, wherein administering dextran sulfate comprises administering the dextran sulfate, or the pharmaceutically acceptable salt thereof, to a subject suffering from an infection or an infectious disease that may cause sepsis in the subject.

3. The method according to claim 1, wherein administering dextran sulfate comprises systemically administering the dextran sulfate, or the pharmaceutically acceptable salt thereof, to the subject.

4. The method according to claim 3, wherein administering dextran sulfate comprises intravenously administering the dextran sulfate, or the pharmaceutically acceptable salt thereof, to the subject.

5. The method according to claim 3, wherein administering dextran sulfate comprises subcutaneously administering the dextran sulfate, or the pharmaceutically acceptable salt thereof, to the subject.

6. The method according to claim 1, wherein the dextran sulfate, or the pharmaceutically acceptable salt thereof, has an average sulfur content in a range of from 15 to 20%.

7. The method according to claim 1, wherein the dextran sulfate, or the pharmaceutically acceptable salt thereof, has a Mn as measured by NMR spectroscopy within a range of from 1850 to 2500 Da.

8. The method according to claim 7, wherein the dextran sulfate, or the pharmaceutically acceptable salt thereof, has a Mn as measured by NMR spectroscopy within a range of from 1850 to 2300 Da.

9. The method according to claim 8, wherein the dextran sulfate, or the pharmaceutically acceptable salt thereof, has a Mn as measured by NMR spectroscopy within a range of from 1850 to 2000 Da.

10. The method according to claim 1, wherein the dextran sulfate, or the pharmaceutically acceptable salt thereof, has an average sulfate number per glucose unit within a range of from 2.5 to 2.8.

11. The method according to claim 10, wherein the dextran sulfate, or the pharmaceutically acceptable salt thereof, has an average sulfate number per glucose unit within a range of from 2.6 to 2.7.

12. The method according to claim 1, wherein the dextran sulfate, or the pharmaceutically acceptable salt thereof, has an average number of glucose units within an interval of from 4.0 to 6.0.

13. The method according to claim 12, wherein the dextran sulfate, or the pharmaceutically acceptable salt thereof, has an average number of glucose units within an interval of from 4.5 to 5.5.

14. The method according to claim 13, wherein the dextran sulfate, or the pharmaceutically acceptable salt thereof, has an average number of glucose units within an interval of from 5.0 to 5.2.

15. The method according to claim 1, wherein the dextran sulfate, or the pharmaceutically acceptable salt thereof, has on average 5.1 glucose units and an average sulfate number per glucose unit of 2.6 to 2.7.

16. The method according to claim 1, wherein administering dextran sulfate comprises administering an aqueous injection solution comprising the dextran sulfate, or the pharmaceutically acceptable salt thereof, to the subject.

17. The method according to claim 1, wherein the pharmaceutically acceptable salt thereof is a sodium salt of dextran sulfate.

* * * * *